United States Patent
Baden et al.

(10) Patent No.: US 6,656,705 B1
(45) Date of Patent: Dec. 2, 2003

(54) SCIELLIN AND USES THEREOF

(75) Inventors: Howard P. Baden, Cambridge, MA (US); Pamela Olson, Chestnut Hill, MA (US); Marie-France Champliaud, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/277,431

(22) Filed: Mar. 26, 1999

Related U.S. Application Data

(60) Provisional application No. 60/079,498, filed on Mar. 26, 1998.

(51) Int. Cl.$^7$ .............................. C12N 1/00; C12N 5/10; C12N 15/12; C12N 15/63; C12P 21/02
(52) U.S. Cl. ................ 435/69.1; 435/320.1; 435/252.3; 435/325; 435/254.11; 536/23.5
(58) Field of Search .............................. 435/69.1, 252.3, 435/254.11, 325, 320.1; 536/23.5

(56) References Cited

U.S. PATENT DOCUMENTS 5,525,336 A   6/1996   Green et al. ................ 424/94.5

FOREIGN PATENT DOCUMENTS

| WO | WO 94 28949 A | 12/1994 |
| WO | WO 95 05396 A | 2/1995 |

OTHER PUBLICATIONS

Champliaud, M.F., et al., "Characterization of the Protein Structure of Sciellin, A Unique Precursor of the Cornified Envelope of Keratinizing Tissues", Journal of Dermatological Science, vol. 16, No. Suppl. 1, Mar. 1998, p. S34 XP001065223.

Baden, Howard P. et al., "Epithelial Cornified envelope Precursors Are in the Hair Follicle and Nail", 1993, The Society for Investigative Dermatology, Inc., 101: 72S–74S.

Champliaud, Marie–France et al., "cDNA Cloning and Characterization of Sciellin, a LIM Domain Protein of the Keratinocyte Cornified Envelope", 1998, The Journal of Biological Chemistry, V. 273, No. 47, pp. 31547–31554.

Kvedar, Joseph C. et al., "Characterization of Sciellin, a Precursor to the Cornified Envelope of Human Keratinocytes", 1991, Differentiation, 49: pp. 195–204.

*Primary Examiner*—Gabriele E. Bugaisky
(74) *Attorney, Agent, or Firm*—Fish & Richardson P.C.

(57) ABSTRACT

The present invention relates to novel epidermal protein, sciellin. Sciellin polypeptides comprise an N-terminal domain, a central domain containing sixteen repeats and a C-terminal LIM domain. Sciellin polypeptides may function as precursors of the cornified envelope of keratinizing tissues. Described herein are isolated and antisense nucleic acids molecules, recombinant expression vectors, host cells and non-human transgenic animals containing an insertion or a disruption of the sciellin gene. Diagnostic, screening and therapeutic methods utilizing the compositions of the invention are also provided.

17 Claims, 8 Drawing Sheets

1
CAGATCCTCCCCAGGGAATCACTACAGGCTGGTTAGCCAAAAAGTCCTGATTTTCTGCTCAATAG
AGGTCCTTACTGGAAGGCAGCATGTCCAATGTTAC 100
1                                    M S N V T 5

101
CTTGAGAAAAATGTCTCCCACAGGAAATGAGATGAAGAGCACCACTCAGGGAACCACACGGAAG
CAGCAGGATTTTCACGAGGTGAACAAAAGAAGAACT 200
6  L R K M S P T G N E M K S T T Q G T T R K Q Q D F H E V N K R
R T 38

201
TTCTTACAGGATAACAGTTGGATAAAGAAACGCCCTGAAGAAGAAAAAGATGAAAATTACGGTA
GGGTGGTGCTCAACCGACATAATTCCCATGATGCAT 300
39 F L Q D N S W I K K R P E E K D E N Y G R V V L N R H N S H
D A L 72

301
TGGACAGGAAAGTAAATGAGAGAGATGTGCCAAAAGCTACAATTAGTCGGTACAGTTCTGATGA
CACTTTGGACAGGATCTCAGACAGAAATGATGCTGC 400
73 D R K V N E R D V P K A T I S R Y S S D D T L D R I S D R N D
A A 105

401
TAAAACATATAAGGCCAATACCTTGGATAACCAACTAACCAATAGGAGCATGTCCATGTTTAGA
TCACTGGAAGTAACAAAGTTGCAACCTGGCGGTTCA 500
106 K T Y K A N T L D N Q L T N R S M S M F R S L E V T K L Q P G
G S 138

501
TTGAATGCCAACACCTCCAACACCATAGCATCCACTTCTGCTACTACTCCTGTAAAGAAGAAGA
GGCAGTCCTGGTTTCCACCGCCCCCTCCAGGTTACA 600
139 L N A N T S N T I A S T S A T T P V K K R Q S W F P P P P P
G Y N 172

FIG. 2A

```
601
ATGCCTCTTCGAGCACAGGAACCAGGAGACGGGAACCAGGTGTTCACCCTCCAATACCTCCAAAG
CCCAGTTCTCCTGTTTCTTCTCCTAACCAGCTGAG  700
  173  A S S S T G T R R R E P G V H P P I P P K P S S P V S S P N
Q L R  205

701
ACAGGATAATAGGCAGATACATCCACCTAAACCAGGTGTATATACAGAAACCAACAGATCTGCT
GAAAGAAATATAAGTGAAGAATTGGATAATCTCATC  800
  206  Q D N R Q I H P P K P G V Y T E T N R S A E R N I S E E L D N
L I  238

801
AAAATGAACAAAAGCTTGAATAGGAATCAAGGTCTTGATAGTCTCTTCAGAGCAAATCCAAAGG
TAGAAGAAAGAGAGAAAAGAGCCAAAAGCCTTGAAA  900
  239  K M N K S L N R N Q G L D S L F R A N P K V E E R E K R A K S
L E S  272

901
GTCTCATCTATATGAGTACCCGGACAGATAAAGATGGCAAAGGAATCCAAAGCCTTGGAAGTCC
GATTAAAGTTAATCAAAGGACTGACAAAAATGAGAA  1000
  273  L I Y M S T R T D K D G K G I Q S L G S P I K V N Q R T D K N
E K  305

1001
AGGAAGACAAAATCTCGAATCTGTTGCTAAAGTGGATGCCAGGACGAATAAAACGAGCAGAAGA
AGTGAAGACCTTGATAATGCTACTGAAGTAAATCCC  1100
  306  G R Q N L E S V A K V D A R T N K T S R R S E D L D N A T E V
N P  338

1101
AAAGGACATGAAAATACCACTGGAAAAAAAGACCTTGATGGGCTTATTAAAGTGGATCCTGAAA
CAAATAAAAATATTACGAGGGGCCAGAGCCTTGATA  1200
  339  K G H E N T T G K K D L D G L I K V D P E T N K N I T R G Q S
L D N  372
```

FIG. 2B

1201
ATCTCATCAAAGTGACCCCTGAAGTAAAGAGAAGTAACCAAGGTTCCAAAGACCTTAATAACTT
CATCAAAGTGTATCCAGGAACAGAAAAAAGTACTGA 1300
373 L I K V T P E V K R S N Q G S K D L N N F I K V Y P G T E K S
T E 405

1301
AGGGGGCCAAAGTCTCGACAGCCTCATTAAAGTGACTCCTGAAAGAAACAGAACTAACCAAGGG
AACCAAGACTTGGAAAATCTTATCAAAGTGATCCCT 1400
406 G G Q S L D S L I K V T P E R N R T N Q G N Q D L E N L I K V
I P 438

1401
TCAGCAAACAAAAGCAGTGAACAAGGTCTTGATGAACATATTAATGTCAGCCCCAAAGCTGTCA
AAAACACTGATGGAAAACAAGATCTTGATAAACTCA 1500
439 S A N K S S E Q G L D E H I N V S P K A V K N T D G K Q D L D
K L I 472

1501
TCAAGGTGAATCCTGAAATTTTCACAAACAACCAAAGAAACCAAGATCTTGCTAACCTCATCAA
AGTAAATCCTGCAGTAATCAGAAACAATCAGAGCCA 1600
473 K V N P E I F T N N Q R N Q D L A N L I K V N P A V I R N N Q
S Q 505

1601
AGACTTGGACAATCTTATTAAAGTGAAACCTTCAGCTCTTAGAAACACTAATCGAGACCAGAAC
CTGGAAAATTTAATTGAAGTAAATTCTCATGTGTCT 1700
506 D L D N L I K V K P S A L R N T N R D Q N L E N L I E V N S H
V S 538

1701
GAAAACAAGAATGGAAGCTCTAACACTGGAGCCAAGCAGGCAGGACCACAGGATACTGTTGTGT
ACACAAGGACATATGTGGAGAATAGTAAATCACCCA 1800
539 E N K N G S S N T G A K Q A G P Q D T V V Y T R T Y V E N S K
S P K 572

```
AGGATGGATATCAGGAGAATATCTCTGGAAAATACATACAAACTGTTTATTCAACTTCTGATAG
GTCTGTCATTGAAAGAGATATGTGCACTTACTGCCG  1900
   573  D G Y Q E N I S G K Y I Q T V Y S T S D R S V I E R D M C T Y
C R   605

1901
AAAACCCTTGGGTGTAGAAACTAAAATGATTTTAGATGAATTACAAATTTGCTGCCATTCTACT
TGCTTTAAGTGTGAAATATGCAAGCAGCCTTTGGAA  2000
   606  K P L G V E T K M I L D E L Q I C C H S T C F K C E I C K Q P L
E   638

2001
AATCTrCAAGCGGGTGATAGTATTTGGATTTATAGACAGACAATACACTGTGAACCTTGCTACTC
TAAAATTATGGCAAAGTGGATTCCATAACTCTGGC  2100
   639  N L Q A G D S I W I Y R Q T I H C E P C Y S K I M A K W I P
668

2101
ACAAGGAAATCAAGATGAAAAGCACTCATTAAGGAATTAAAGTTACAAGTTTTATCTTAATAA
TATGTAATCTAGAAAAGCTTTCACATTGAAGATCAAC  2200

2201
TCTTGTACAAAATTAACAATTCTGTTATTGCATAAGTAATCTAATTGTCTTCAATAAGGTCACA
CACATAAAAAGAGCCATCTGGTCTCTGGCTAGAGTT  2300

2301  AGCAATAAAAAGTTCAAATGGTTCCAGAAAAAAAAAAAAAAAAAAA  2347
```

FIG. 2D

MSNVTLRKMS PTGNEMKSTT QGTTRKQQDF HEVNKRRTFL QDNSWIKKRP
EEEKDENYGR VVLNRHNSHD ALDRKVNERD VPKATISRYS SDDTLDRISD
RNDAAKTYKA NTLDNQLTNR SMSMFRSLEV TKLQPGGSLN ANTSNTIAST
SATTPVKKR QSWFPPPPPG YNASSSTGTR RREPGVHPPI PPKPSSPVSS
PNQLRQDNRQ IHPPKPGVYT ETNRSAERNI

SEELDNLIKMN KSLNR
NQGLDSLFRA NPKVEEREKR
AKSLESLIYMS TRTDKDGKG
IQSLGSPIKV NQRTDKNEKG
RQNLESVAKV DARTNKTSRR
SEDLDNATEV NPKGHENTTG
KKDLDGLIKV DPETNKNITR
GQSLDNLIKV TPEVKRSNQG
SKDLNNFIKV YPGTEKSTEG
GQSLDSLIKV TPERNRTNQG
NQDLENLIKV IPSANK<u>SSE</u>
 QGLDEHINVS PKAVKNTTG
KQDLDKLIKV NPEIFTNNQR
NQDLANLIKV NPAVI NNQ
SQDLDNLIKV KPSALRNTNR
DQNLENLIEV NSHVSENKNG

SSNTGAKQAG PQDTVVYTRT YVENSKSPKD GYQENISGKY IQTVYSTSDR
SVIERDMQTY QRKPLGVETK MILDELQIQQ HSTQFKQEIQ KQPLENLQAG
DSIWIYRQTI HQEPQYSKIM AKW

FIG. 3

```
600 MDTYQRKPLGVETKMILDELQICQHSTQFKQEIQKQPLENLQAGDSIWIYRQTIHQEPQYSKI 662
391 ITTYQNFEIRDCPKITLEHLGICQHEYQFKQGIQSKPMGDLL--DQIFIHRDTIHQGKQYEKL 451
291 VDTYQSHEIQDCPKITLEHLGICQHEYQFKQGIQNKPMGDLL--DQIFIHRDTIHQGKQYEKL 351
271 IQSYQNNILGKGAAMIIESLGLCYHQFKQVAQECDLGGSSSGAEVRIRNHQLYQNDQY     330
347 RQAHQNEELGRGAAMIVESLNLFYHLAQFKQYQKTSLGSGATGADVRVRDGRLHQQTQYS    407
 40 QVEQRKPIGADSKEVHYKNRFW-HDTQFRQAKQLQPLAN                         77
352 SQGKQNQPLA-RAQPAVRALGQLFHITQFTQHQQQQLQ----GQQFYSLEGAPYQEGQYTDT 435
384 LQGRQHQPLA-RAQPAVRALGQLFHIAQFTQHQAQQLQ----GQQFYSLEGAPYQEGQYTDT 443
```

FIG. 5

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 2347 base pairs
      (B) TYPE: nucleic acid
      (C) STRANDEDNESS: single
      (D) TOPOLOGY: linear (ix) FEATURE:
      (A) NAME/KEY: Coding Sequence
      (B) LOCATION: 87...2090

(xi) SEQUENCE DESCRIPTION: SEQ ID NO:1:

```
CAGATCCTCC CCAGGGAATC ACTACAGGCT GGTTAGCCAA AAAGTCCTGA TTTTCTGCTC        60

AATAGAGGTC CTTACTGGAA GGCAGC ATG TCC AAT GTT ACC TTG AGA AAA ATG        113
                            Met Ser Asn Val Thr Leu Arg Lys Met
                             1               5

TCT CCC ACA GGA AAT GAG ATG AAG AGC ACC ACT CAG GGA ACC ACA CGG         161
Ser Pro Thr Gly Asn Glu Met Lys Ser Thr Thr Gln Gly Thr Thr Arg
 10              15                  20                  25

AAG CAG CAG GAT TTT CAC GAG GTG AAC AAA AGA AGA ACT TTC TTA CAG         209
Lys Gln Gln Asp Phe His Glu Val Asn Lys Arg Arg Thr Phe Leu Gln
                 30                  35                  40

GAT AAC AGT TGG ATA AAG AAA CGC CCT GAA GAA GAA AAA GAT GAA AAT         257
Asp Asn Ser Trp Ile Lys Lys Arg Pro Glu Glu Glu Lys Asp Glu Asn
             45                  50                  55

TAC GGT AGG GTG GTG CTC AAC CGA CAT AAT TCC CAT GAT GCA TTG GAC         305
Tyr Gly Arg Val Val Leu Asn Arg His Asn Ser His Asp Ala Leu Asp
         60                  65                  70

AGG AAA GTA AAT GAG AGA GAT GTG CCA AAA GCT ACA ATT AGT CGG TAC         353
Arg Lys Val Asn Glu Arg Asp Val Pro Lys Ala Thr Ile Ser Arg Tyr
 75                  80                  85

AGT TCT GAT GAC ACT TTG GAC AGG ATC TCA GAC AGA AAT GAT GCT GCT         401
Ser Ser Asp Asp Thr Leu Asp Arg Ile Ser Asp Arg Asn Asp Ala Ala
 90                  95                 100                 105

AAA ACA TAT AAG GCC AAT ACC TTG GAT AAC CAA CTA ACC AAT AGG AGC         449
Lys Thr Tyr Lys Ala Asn Thr Leu Asp Asn Gln Leu Thr Asn Arg Ser
                110                 115                 120

ATG TCC ATG TTT AGA TCA CTG GAA GTA ACA AAG TTG CAA CCT GGC GGT         497
Met Ser Met Phe Arg Ser Leu Glu Val Thr Lys Leu Gln Pro Gly Gly
            125                 130                 135

TCA TTG AAT GCC AAC ACC TCC AAC ACC ATA GCA TCC ACT TCT GCT ACT         545
Ser Leu Asn Ala Asn Thr Ser Asn Thr Ile Ala Ser Thr Ser Ala Thr
        140                 145                 150

ACT CCT GTA AAG AAG AAG AGG CAG TCC TGG TTT CCA CCG CCC CCT CCA         593
Thr Pro Val Lys Lys Lys Arg Gln Ser Trp Phe Pro Pro Pro Pro Pro
155                 160                 165

GGT TAC AAT GCC TCT TCG AGC ACA GGA ACC AGG AGA CGG GAA CCA GGT         641
Gly Tyr Asn Ala Ser Ser Ser Thr Gly Thr Arg Arg Arg Glu Pro Gly
170                 175                 180                 185

GTT CAC CCT CCA ATA CCT CCA AAG CCC AGT TCT CCT GTT TCT TCT CCT         689
Val His Pro Pro Ile Pro Pro Lys Pro Ser Ser Pro Val Ser Ser Pro
                190                 195                 200

AAC CAG CTG AGA CAG GAT AAT AGG CAG ATA CAT CCA CCT AAA CCA GGT         737
Asn Gln Leu Arg Gln Asp Asn Arg Gln Ile His Pro Pro Lys Pro Gly
            205                 210                 215
```

```
GTA TAT ACA GAA ACC AAC AGA TCT GCT GAA AGA AAT ATA AGT GAA GAA      785
Val Tyr Thr Glu Thr Asn Arg Ser Ala Glu Arg Asn Ile Ser Glu Glu
        220                 225                 230

TTG GAT AAT CTC ATC AAA ATG AAC AAA AGC TTG AAT AGG AAT CAA GGT      833
Leu Asp Asn Leu Ile Lys Met Asn Lys Ser Leu Asn Arg Asn Gln Gly
        235                 240                 245

CTT GAT AGT CTC TTC AGA GCA AAT CCA AAG GTA GAA GAA AGA GAG AAA      881
Leu Asp Ser Leu Phe Arg Ala Asn Pro Lys Val Glu Glu Arg Glu Lys
250                 255                 260                 265

AGA GCC AAA AGC CTT GAA AGT CTC ATC TAT ATG AGT ACC CGG ACA GAT      929
Arg Ala Lys Ser Leu Glu Ser Leu Ile Tyr Met Ser Thr Arg Thr Asp
                270                 275                 280

AAA GAT GGC AAA GGA ATC CAA AGC CTT GGA AGT CCG ATT AAA GTT AAT      977
Lys Asp Gly Lys Gly Ile Gln Ser Leu Gly Ser Pro Ile Lys Val Asn
            285                 290                 295

CAA AGG ACT GAC AAA AAT GAG AAA GGA AGA CAA AAT CTC GAA TCT GTT     1025
Gln Arg Thr Asp Lys Asn Glu Lys Gly Arg Gln Asn Leu Glu Ser Val
        300                 305                 310

GCT AAA GTG GAT GCC AGG ACG AAT AAA ACG AGC AGA AGA AGT GAA GAC     1073
Ala Lys Val Asp Ala Arg Thr Asn Lys Thr Ser Arg Arg Ser Glu Asp
315                 320                 325

CTT GAT AAT GCT ACT GAA GTA AAT CCC AAA GGA CAT GAA AAT ACC ACT     1121
Leu Asp Asn Ala Thr Glu Val Asn Pro Lys Gly His Glu Asn Thr Thr
330                 335                 340                 345

GGA AAA AAA GAC CTT GAT GGG CTT ATT AAA GTG GAT CCT GAA ACA AAT     1169
Gly Lys Lys Asp Leu Asp Gly Leu Ile Lys Val Asp Pro Glu Thr Asn
                350                 355                 360

AAA AAT ATT ACG AGG GGC CAG AGC CTT GAT AAT CTC ATC AAA GTG ACC     1217
Lys Asn Ile Thr Arg Gly Gln Ser Leu Asp Asn Leu Ile Lys Val Thr
            365                 370                 375

CCT GAA GTA AAG AGA AGT AAC CAA GGT TCC AAA GAC CTT AAT AAC TTC     1265
Pro Glu Val Lys Arg Ser Asn Gln Gly Ser Lys Asp Leu Asn Asn Phe
        380                 385                 390

ATC AAA GTG TAT CCA GGA ACA GAA AAA AGT ACT GAA GGG GGC CAA AGT     1313
Ile Lys Val Tyr Pro Gly Thr Glu Lys Ser Thr Glu Gly Gly Gln Ser
        395                 400                 405

CTC GAC AGC CTC ATT AAA GTG ACT CCT GAA AGA AAC AGA ACT AAC CAA     1361
Leu Asp Ser Leu Ile Lys Val Thr Pro Glu Arg Asn Arg Thr Asn Gln
410                 415                 420                 425

GGG AAC CAA GAC TTG GAA AAT CTT ATC AAA GTG ATC CCT TCA GCA AAC     1409
Gly Asn Gln Asp Leu Glu Asn Leu Ile Lys Val Ile Pro Ser Ala Asn
                430                 435                 440

AAA AGC AGT GAA CAA GGT CTT GAT GAA CAT ATT AAT GTC AGC CCC AAA     1457
Lys Ser Ser Glu Gln Gly Leu Asp Glu His Ile Asn Val Ser Pro Lys
            445                 450                 455

GCT GTC AAA AAC ACT GAT GGA AAA CAA GAT CTT GAT AAA CTC ATC AAG     1505
Ala Val Lys Asn Thr Asp Gly Lys Gln Asp Leu Asp Lys Leu Ile Lys
        460                 465                 470

GTG AAT CCT GAA ATT TTC ACA AAC AAC CAA AGA AAC CAA GAT CTT GCT     1553
Val Asn Pro Glu Ile Phe Thr Asn Asn Gln Arg Asn Gln Asp Leu Ala
        475                 480                 485

AAC CTC ATC AAA GTA AAT CCT GCA GTA ATC AGA AAC AAT CAG AGC CAA     1601
Asn Leu Ile Lys Val Asn Pro Ala Val Ile Arg Asn Asn Gln Ser Gln
490                 495                 500                 505

GAC TTG GAC AAT CTT ATT AAA GTG AAA CCT TCA GCT CTT AGA AAC ACT     1649
Asp Leu Asp Asn Leu Ile Lys Val Lys Pro Ser Ala Leu Arg Asn Thr
                510                 515                 520

AAT CGA GAC CAG AAC CTG GAA AAT TTA ATT GAA GTA AAT TCT CAT GTG     1697
Asn Arg Asp Gln Asn Leu Glu Asn Leu Ile Glu Val Asn Ser His Val
```

-continued

```
              525                     530                     535
TCT GAA AAC AAG AAT GGA AGC TCT AAC ACT GGA GCC AAG CAG GCA GGA        1745
Ser Glu Asn Lys Asn Gly Ser Ser Asn Thr Gly Ala Lys Gln Ala Gly
            540                     545                     550

CCA CAG GAT ACT GTT GTG TAC ACA AGG ACA TAT GTG GAG AAT AGT AAA        1793
Pro Gln Asp Thr Val Val Tyr Thr Arg Thr Tyr Val Glu Asn Ser Lys
        555                     560                     565

TCA CCC AAG GAT GGA TAT CAG GAG AAT ATC TCT GGA AAA TAC ATA CAA        1841
Ser Pro Lys Asp Gly Tyr Gln Glu Asn Ile Ser Gly Lys Tyr Ile Gln
570                     575                     580                     585

ACT GTT TAT TCA ACT TCT GAT AGG TCT GTC ATT GAA AGA GAT ATG TGC        1889
Thr Val Tyr Ser Thr Ser Asp Arg Ser Val Ile Glu Arg Asp Met Cys
                590                     595                     600

ACT TAC TGC CGA AAA CCC TTG GGT GTA GAA ACT AAA ATG ATT TTA GAT        1937
Thr Tyr Cys Arg Lys Pro Leu Gly Val Glu Thr Lys Met Ile Leu Asp
            605                     610                     615

GAA TTA CAA ATT TGC TGC CAT TCT ACT TGC TTT AAG TGT GAA ATA TGC        1985
Glu Leu Gln Ile Cys Cys His Ser Thr Cys Phe Lys Cys Glu Ile Cys
        620                     625                     630

AAG CAG CCT TTG GAA AAT CTT CAA GCG GGT GAT AGT ATT TGG ATT TAT        2033
Lys Gln Pro Leu Glu Asn Leu Gln Ala Gly Asp Ser Ile Trp Ile Tyr
635                     640                     645

AGA CAG ACA ATA CAC TGT GAA CCT TGC TAC TCT AAA ATT ATG GCA AAG        2081
Arg Gln Thr Ile His Cys Glu Pro Cys Tyr Ser Lys Ile Met Ala Lys
650                     655                     660                     665

TGG ATT CCA TAACTCTGGC ACAAGGAAAT CAAGATGAAA AGCACTCATT AAGGAATTA      2139
Trp Ile Pro

AAGTTACAAG TTTTATCTTA ATAATATGTA ATCTAGAAAA GCTTTCACAT TGAAGATCAA      2199

CTCTTGTACA AAATTAACAA TTCTGTTATT GCATAAGTAA TCTAATTGTC TTCAATAAGG      2259

TCACACACAT AAAAAGAGCC ATCTGGTCTC TGGCTAGAGT TAGCAATAAA AAGTTCAAAT      2319

GGTTCCAGAA AAAAAAAAAA AAAAAAA                                          2347
```

(2) INFORMATION FOR SEQ ID NO:2:

(i) SEQUENCE CHARACTERISTICS:
        (A) LENGTH: 668 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:2:

```
Met Ser Asn Val Thr Leu Arg Lys Met Ser Pro Thr Gly Asn Glu Met
1               5                   10                  15

Lys Ser Thr Thr Gln Gly Thr Thr Arg Lys Gln Gln Asp Phe His Glu
            20                  25                  30

Val Asn Lys Arg Arg Thr Phe Leu Gln Asp Asn Ser Trp Ile Lys Lys
        35                  40                  45

Arg Pro Glu Glu Lys Asp Glu Asn Tyr Gly Arg Val Val Leu Asn
    50                  55                  60

Arg His Asn Ser His Asp Ala Leu Asp Arg Lys Val Asn Glu Arg Asp
65                  70                  75                  80

Val Pro Lys Ala Thr Ile Ser Arg Tyr Ser Ser Asp Thr Leu Asp
                85                  90                  95

Arg Ile Ser Asp Arg Asn Asp Ala Ala Lys Thr Tyr Lys Ala Asn Thr
                100                 105                 110
```

-continued

```
Leu Asp Asn Gln Leu Thr Asn Arg Ser Met Ser Met Phe Arg Ser Leu
            115                 120                 125
Glu Val Thr Lys Leu Gln Pro Gly Gly Ser Leu Asn Ala Asn Thr Ser
130                 135                 140
Asn Thr Ile Ala Ser Thr Ser Ala Thr Thr Pro Val Lys Lys Lys Arg
145                 150                 155                 160
Gln Ser Trp Phe Pro Pro Pro Pro Gly Tyr Asn Ala Ser Ser Ser
                165                 170                 175
Thr Gly Thr Arg Arg Arg Glu Pro Gly Val His Pro Pro Ile Pro Pro
            180                 185                 190
Lys Pro Ser Ser Pro Val Ser Ser Pro Asn Gln Leu Arg Gln Asp Asn
            195                 200                 205
Arg Gln Ile His Pro Pro Lys Pro Gly Val Tyr Thr Glu Thr Asn Arg
210                 215                 220
Ser Ala Glu Arg Asn Ile Ser Glu Glu Leu Asp Asn Leu Ile Lys Met
225                 230                 235                 240
Asn Lys Ser Leu Asn Arg Asn Gln Gly Leu Asp Ser Leu Phe Arg Ala
                245                 250                 255
Asn Pro Lys Val Glu Glu Arg Glu Lys Arg Ala Lys Ser Leu Glu Ser
            260                 265                 270
Leu Ile Tyr Met Ser Thr Arg Thr Asp Lys Asp Gly Lys Gly Ile Gln
            275                 280                 285
Ser Leu Gly Ser Pro Ile Lys Val Asn Gln Arg Thr Asp Lys Asn Glu
            290                 295                 300
Lys Gly Arg Gln Asn Leu Glu Ser Val Ala Lys Val Asp Ala Arg Thr
305                 310                 315                 320
Asn Lys Thr Ser Arg Arg Ser Glu Asp Leu Asp Asn Ala Thr Glu Val
                325                 330                 335
Asn Pro Lys Gly His Glu Asn Thr Thr Gly Lys Lys Asp Leu Asp Gly
            340                 345                 350
Leu Ile Lys Val Asp Pro Glu Thr Asn Lys Asn Ile Thr Arg Gly Gln
            355                 360                 365
Ser Leu Asp Asn Leu Ile Lys Val Thr Pro Glu Val Lys Arg Ser Asn
370                 375                 380
Gln Gly Ser Lys Asp Leu Asn Asn Phe Ile Lys Val Tyr Pro Gly Thr
385                 390                 395                 400
Glu Lys Ser Thr Glu Gly Gly Gln Ser Leu Asp Ser Leu Ile Lys Val
                405                 410                 415
Thr Pro Glu Arg Asn Arg Thr Asn Gln Gly Asn Gln Asp Leu Glu Asn
            420                 425                 430
Leu Ile Lys Val Ile Pro Ser Ala Asn Lys Ser Ser Glu Gln Gly Leu
            435                 440                 445
Asp Glu His Ile Asn Val Ser Pro Lys Ala Val Lys Asn Thr Asp Gly
            450                 455                 460
Lys Gln Asp Leu Asp Lys Leu Ile Lys Val Asn Pro Glu Ile Phe Thr
465                 470                 475                 480
Asn Asn Gln Arg Asn Gln Asp Leu Ala Asn Leu Ile Lys Val Asn Pro
                485                 490                 495
Ala Val Ile Arg Asn Asn Gln Ser Gln Asp Leu Asp Asn Leu Ile Lys
            500                 505                 510
Val Lys Pro Ser Ala Leu Arg Asn Thr Asn Arg Asp Gln Asn Leu Glu
            515                 520                 525
```

```
Asn Leu Ile Glu Val Asn Ser His Val Ser Glu Asn Lys Asn Gly Ser
        530                 535                 540

Ser Asn Thr Gly Ala Lys Gln Ala Gly Pro Gln Asp Thr Val Tyr
545                 550                 555                 560

Thr Arg Thr Tyr Val Glu Asn Ser Lys Ser Pro Lys Asp Gly Tyr Gln
                    565                 570                 575

Glu Asn Ile Ser Gly Lys Tyr Ile Gln Thr Val Tyr Ser Thr Ser Asp
                580                 585                 590

Arg Ser Val Ile Glu Arg Asp Met Cys Thr Tyr Cys Arg Lys Pro Leu
                595                 600                 605

Gly Val Glu Thr Lys Met Ile Leu Asp Glu Leu Gln Ile Cys Cys His
                610                 615                 620

Ser Thr Cys Phe Lys Cys Glu Ile Cys Lys Gln Pro Leu Glu Asn Leu
625                 630                 635                 640

Gln Ala Gly Asp Ser Ile Trp Ile Tyr Arg Gln Thr Ile His Cys Glu
                645                 650                 655

Pro Cys Tyr Ser Lys Ile Met Ala Lys Trp Ile Pro
                660                 665

(2) INFORMATION FOR SEQ ID NO:3:

(i) SEQUENCE CHARACTERISTICS:
        (A) LENGTH: 63 amino acids
        (B) TYPE: amino acid
        (D) TOPOLOGY: linear (ii) MOLECULE TYPE: peptide (xi) SEQUENCE DESCRIPTION: SEQ ID NO:3:

Met Cys Thr Tyr Cys Arg Lys Pro Leu Gly Val Glu Thr Lys Met Ile
1               5                   10                  15

Leu Asp Glu Leu Gln Ile Cys Cys His Ser Thr Cys Phe Lys Cys Glu
                20                  25                  30

Ile Cys Lys Gln Pro Leu Glu Asn Leu Gln Ala Gly Asp Ser Ile Trp
            35                  40                  45

Ile Tyr Arg Gln Thr Ile His Cys Glu Pro Cys Tyr Ser Lys Ile
        50                  55                  60

(2) INFORMATION FOR SEQ ID NO:4:

(i) SEQUENCE CHARACTERISTICS:
        (A) LENGTH: 61 amino acids
        (B) TYPE: amino acid
        (D) TOPOLOGY: linear (ii) MOLECULE TYPE: peptide (xi) SEQUENCE DESCRIPTION: SEQ ID NO:4:

Ile Cys Thr Tyr Cys Asn Arg Glu Ile Arg Asp Cys Pro Lys Ile Thr
1               5                   10                  15

Leu Glu His Leu Gly Ile Cys Cys His Glu Tyr Cys Phe Lys Cys Gly
                20                  25                  30

Ile Cys Ser Lys Pro Met Gly Asp Leu Leu Asp Gln Ile Phe Ile His
            35                  40                  45

Arg Asp Thr Ile His Cys Gly Lys Cys Tyr Glu Lys Leu
        50                  55                  60

(2) INFORMATION FOR SEQ ID NO:5:

(i) SEQUENCE CHARACTERISTICS:
```

(A) LENGTH: 61 amino acids
        (B) TYPE: amino acid
        (D) TOPOLOGY: linear (ii) MOLECULE TYPE: peptide (xi) SEQUENCE DESCRIPTION: SEQ ID NO:5:

Val Cys Thr Tyr Cys Ser His Glu Ile Gln Asp Cys Pro Lys Ile Thr
 1               5                  10                  15

Leu Glu His Leu Gly Ile Cys Cys His Glu Tyr Cys Phe Lys Cys Gly
             20                  25                  30

Ile Cys Asn Lys Pro Met Gly Asp Leu Leu Asp Gln Ile Phe Ile His
         35                  40                  45

Arg Asp Thr Ile His Cys Gly Lys Cys Tyr Glu Lys Leu
     50                  55                  60

(2) INFORMATION FOR SEQ ID NO:6:

(i) SEQUENCE CHARACTERISTICS:
        (A) LENGTH: 60 amino acids
        (B) TYPE: amino acid
        (D) TOPOLOGY: linear (ii) MOLECULE TYPE: peptide (xi) SEQUENCE DESCRIPTION: SEQ ID NO:6:

Ile Cys Ser Tyr Cys Asn Asn Ile Leu Gly Lys Gly Ala Ala Met Ile
 1               5                  10                  15

Ile Glu Ser Leu Gly Leu Cys Tyr His Leu His Cys Phe Lys Cys Val
             20                  25                  30

Ala Cys Glu Cys Asp Leu Gly Gly Ser Ser Ser Gly Ala Glu Val Arg
         35                  40                  45

Ile Arg Asn His Gln Leu Tyr Cys Asn Asp Cys Tyr
     50                  55                  60

(2) INFORMATION FOR SEQ ID NO:7:

(i) SEQUENCE CHARACTERISTICS:
        (A) LENGTH: 61 amino acids
        (B) TYPE: amino acid
        (D) TOPOLOGY: linear (ii) MOLECULE TYPE: peptide (xi) SEQUENCE DESCRIPTION: SEQ ID NO:7:

Arg Cys Ala His Cys Asn Glu Glu Leu Gly Arg Gly Ala Ala Met Ile
 1               5                  10                  15

Val Glu Ser Leu Asn Leu Phe Tyr His Leu Ala Cys Phe Lys Cys Tyr
             20                  25                  30

Val Cys Lys Thr Ser Leu Gly Ser Gly Ala Thr Gly Ala Asp Val Arg
         35                  40                  45

Val Arg Asp Gly Arg Leu His Cys Gln Thr Cys Tyr Ser
     50                  55                  60

(2) INFORMATION FOR SEQ ID NO:8:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (xi) SEQUENCE DESCRIPTION: SEQ ID NO:8:

```
Cys Val Glu Cys Arg Lys Pro Ile Gly Ala Asp Ser Lys Glu Val His
 1               5                  10                  15

Tyr Lys Asn Arg Phe Trp His Asp Thr Cys Phe Arg Cys Ala Lys Cys
                20                  25                  30

Leu Gln Pro Leu Ala Asn
                35
```

(2) INFORMATION FOR SEQ ID NO:9:

(i) SEQUENCE CHARACTERISTICS:
        (A) LENGTH: 58 amino acids
        (B) TYPE: amino acid
        (D) TOPOLOGY: linear (ii) MOLECULE TYPE: peptide (xi) SEQUENCE DESCRIPTION: SEQ ID NO:9:

```
Ser Cys Gly Lys Cys Asn Gln Pro Leu Ala Arg Ala Gln Pro Ala Val
 1               5                  10                  15

Arg Ala Leu Gly Gln Leu Phe His Ile Thr Cys Phe Thr Cys His Gln
                20                  25                  30

Cys Gln Gln Gln Leu Gln Gly Gln Gln Phe Tyr Ser Leu Glu Gly Ala
                35                  40                  45

Pro Tyr Cys Glu Gly Cys Tyr Thr Asp Thr
                50                  55
```

(2) INFORMATION FOR SEQ ID NO:10:

(i) SEQUENCE CHARACTERISTICS:
        (A) LENGTH: 58 amino acids
        (B) TYPE: amino acid
        (D) TOPOLOGY: linear (ii) MOLECULE TYPE: peptide (xi) SEQUENCE DESCRIPTION: SEQ ID NO:10:

```
Leu Cys Gly Arg Cys His Gln Pro Leu Ala Arg Ala Gln Pro Ala Val
 1               5                  10                  15

Arg Ala Leu Gly Gln Leu Phe His Ile Ala Cys Phe Thr Cys His Gln
                20                  25                  30

Cys Ala Gln Gln Leu Gln Gly Gln Gln Phe Tyr Ser Leu Glu Gly Ala
                35                  40                  45

Pro Tyr Cys Glu Gly Cys Tyr Thr Asp Thr
                50                  55
```

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
ACGACTCCTG GAGCCCGTCA GTAT                                    24
```

(2) INFORMATION FOR SEQ ID NO:12:

(i) SEQUENCE CHARACTERISTICS:
        (A) LENGTH: 24 base pairs
        (B) TYPE: nucleic acid (C) STRANDEDNESS: single
            (D) TOPOLOGY: linear (ii) MOLECULE TYPE: cDNA (xi) SEQUENCE DESCRIPTION: SEQ ID NO:12:

ACCAACTGGT AATGGTAGCG ACCG                                          24

(2) INFORMATION FOR SEQ ID NO:13:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:13:

CTTCAGGGGT CACTTTGATG AGAT                                          24

(2) INFORMATION FOR SEQ ID NO:14:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:14:

ATCAAGGCTC TGGCCCCTCG TAAT                                          24

(2) INFORMATION FOR SEQ ID NO:15:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:15:

AACAATCAGA GCCAAGACTT GGAC                                          24

(2) INFORMATION FOR SEQ ID NO:16:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:16:

GAAACACTAA TCGAGACCAG AACCTGG                                       27

(2) INFORMATION FOR SEQ ID NO:17:

(i) SEQUENCE CHARACTERISTICS:
            (A) LENGTH: 60 amino acids
            (B) TYPE: amino acid
            (D) TOPOLOGY: linear (ii) MOLECULE TYPE: peptide

```
    (ix) FEATURE:
         (B) LOCATION: 2...3
         (D) OTHER INFORMATION: where Xaa at positions 2 and 3 may be
         any amino acid
         (B) LOCATION: 5...24
         (D) OTHER INFORMATION: where Xaa at positions 5 through 24
         may be any amino acid; any 4 of these amino acids may be
         absent or present
         (B) LOCATION: 26...27
         (D) OTHER INFORMATION: where Xaa at positions 26 and 27 may be
         any amino acid
         (B) LOCATION: 29...30
         (D) OTHER INFORMATION: where Xaa at positions 29 and 30 may be
         any amino acid
         (B) LOCATION: 32...33
         (D) OTHER INFORMATION: where Xaa at positions 32 and 33 may be
         any amino acid
         (B) LOCATION: 35...55
         (D) OTHER INFORMATION: where Xaa at positions 35 through 55
         may be any amino acid; any 5 of these amino acids may be
         absent or present
         (B) LOCATION: 57...59
         (D) OTHER INFORMATION: where Xaa at positions 57 through 59
         may be any amino acid; any 1 of these amino acids may be
         absent or present
         (B) LOCATION: 60...60
         (D) OTHER INFORMATION: where Xaa at position 60 may be any
         one of Cys, His or Asp (xi) SEQUENCE DESCRIPTION: SEQ ID NO:17:

Cys Xaa Xaa Cys Xaa Xaa Xaa Xaa Xaa Xaa Xaa Xaa Xaa Xaa Xaa
 1               5                  10                  15

Xaa Xaa Xaa Xaa Xaa Xaa Xaa Xaa His Xaa Xaa Cys Xaa Xaa Cys Xaa
            20                  25                  30

Xaa Cys Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Cys Xaa Xaa Xaa Xaa
    50                  55                  60

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

GCAAGCGGGT GATAGTATTT GGAT                                            24

(2) INFORMATION FOR SEQ ID NO:19:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

GTTCCATATG GAAAATACCA CTGGAAAAAA AGAC                                 34

(2) INFORMATION FOR SEQ ID NO:20:

(i) SEQUENCE CHARACTERISTICS:
        (A) LENGTH: 32 base pairs
        (B) TYPE: nucleic acid
```

(C) STRANDEDNESS: single
        (D) TOPOLOGY: linear (ii) MOLECULE TYPE: cDNA (xi) SEQUENCE DESCRIPTION: SEQ ID NO:20:

TCCCGCGGTT ACTTGGCTCC AGTGTTAGAG CT                                32

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

TTTGGAACCT TGGTTACTTC T                                            21

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

GGCTCTGAGA CTAAAATAAT GTCT                                         24

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

CTTCAGGGGT CACTTTGATG AGAT                                         24

(2) INFORMATION FOR SEQ ID NO:24:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

AGCGGCCAAA TGGCTCTGAG AC                                           22

(2) INFORMATION FOR SEQ ID NO:25:

(i) SEQUENCE CHARACTERISTICS:
        (A) LENGTH: 15 amino acids
        (B) TYPE: amino acid
        (D) TOPOLOGY: linear (ii) MOLECULE TYPE: peptide -continued (xi) SEQUENCE DESCRIPTION: SEQ ID NO:25:

Ser Ser Glu Gln Gly Leu Asp Glu His Ile Asn Val Ser Pro Lys
1               5                   10                  15

(2) INFORMATION FOR SEQ ID NO:26:

(i) SEQUENCE CHARACTERISTICS:
      (A) LENGTH: 16 amino acids
      (B) TYPE: amino acid
      (D) TOPOLOGY: linear (ii) MOLECULE TYPE: peptide (xi) SEQUENCE DESCRIPTION: SEQ ID NO:26:

Gln Pro Leu Glu Asn Leu Gln Ala Gly Asp Ser Ile Trp Ile Tyr Arg
1               5                   10                  15

SCIELLIN AND USES THEREOF

CROSS-REFERENCE TO RELATED APPLICATION

This application claims benefit from U.S. provisional application Ser. No. 60/079,498, filed Mar. 26, 1998.

BACKGROUND OF THE INVENTION

The cornified envelope is a fifteen (15) nm thick insoluble protein layer that is formed under the plasma membrane in the upper layers of epidermis and keratinizing stratified epithelium (Reichert, U. et al. (1993) *Molecular Biology of the Skin*, 107–150). It appears to play a major role in the physical barrier properties of the stratum corneum (Elias, P. M. and D. S. Friend (1975) *J. Cell. Biol*. 65:180–191). The envelope is formed from several precursor proteins by the calcium dependent enzyme transglutaminase, which catalyzes formation of ε-(γ-glutamyl) lysine crosslinks (Polakowska, R. R. and L. A. Goldsmith (1991) *Physiology, Biochemistry and Molecular Biology of the Skin*, 168–201) that are resistant to proteolytic digestion. It has been postulated that crosslinking of an envelope related protein, involucrin, to the plasma membrane is a first step in envelope assembly (Ishida-Yamamoto, A. et al. (1997) *J. Invest. Dermatol*. 108:12–16). This is followed by crosslinking of the less abundant precursors such as SPRR proteins, elafin, envoplakin, filaggrin, keratin filaments and cystatin a (Steinert, P. M. and L. N. Marekov (1995) *J. Biol. Chem*. 270:17702–17711; Takahashi, H. et al. (1997) *J. Invest. Dermatol*. 108:843–847; Ruhrberg, C. et al. (1996) *J. Cell. Biol*. 134:715–729; Takahashi, M. et al. (1996) *Arch. Biochem. and Biophys*. 329:123–126). Finally loricrin covers the cytoplasmic side of the envelope (Candi, E. et al. (1995) *J. Biol. Chem*.270: 26382–26390).

Several reports have suggested that multiple components are necessary for envelope structure and function. Involucrin for example acts as the framework for the attachment of other envelope components and is covalently linked to the lipids which are important components of the barrier of stratum corneum cells (Downing, D. T. (1992) *J. Lipid Res*. 33:301–313). The pancornulin proteins have been shown to act as molecular bridges and are able to cross-link with two different proteins (Li, V. W. et al. (1996) *Dermatology Clinics* 745–751). Loricrin can impart flexibility as a result of its high glycine content and insolubility from disulfide bonds.

Gene mutation and knockout studies have been used to gather information on the function of epidermal proteins, with the keratins being the most well known (Fuchs, E. et al. (1992) *PNAS* 89:6906–6910; Vassar, R. et al. (1991) *Cell* 64:365–380). Only one study of envelope related proteins has been reported, a loricrin knockout mouse (deviragh, P. A. et al. (1996) *J. Invest. Dermatol*. 106:844; deviragh, P. A. et al. (1997) *J. Invest. Dermatol*. 108:555). Heterozygous mice are normal, while homozygotes have abnormal skin during the first few days, but the animals appear normal as adults However, the mice have a defect in barrier function and respond abnormally to the application of some chemicals. A mutation of the loricrin gene has been observed in patients with a rare autosomal dominant palmoplantar keratoderma, Vohwinkel's Keratoderma, as well as in Progressive, Symmetric Erythrokeratoderma (Ishida-Yamamoto, A. et al. (1997)*J. Invest. Dermatol*. 108:12–16). Loss of epidermnal transglutaminase activity from mutations in the gene results in the human disease, lamellar ichthyosis, which is characterized by ia thickened stratum corneum, disturbed epidermal keratinization and inflammatory changes (Huber, M. et al. (1995) *Science* 267:525–528).

SUMMARY OF THE INVENTION

The present invention is based, in part, on the discovery of the gene which encodes the epidermal protein, sciellin. Accordingly, the present invention features a purified or isolated preparation or a recombinant preparation of sciellin, or a sciellin polypeptide.

In a preferred embodiment, sciellin has at least 60% to about 70%, more preferably at least about 80%, even more preferably at least about 90% to about 95%, and most preferably at least about 99% sequence identity with human sciellin, e.g., the human sciellin of SEQ ID NO:2. Sciellin can be identical to a human sciellin sequence, e.g., that of SEQ ID NO:2. In another embodiment, sciellin is encoded by a nucleic acid molecule which hybridizes under stringent conditions to a nucleic acid molecule of the nucleic acid sequence shown in SEQ ID NO:1. In addition, sciellin can have substantially the same electrophoretic mobility as human sciellin, e.g., it appears as an electrophoretic band of about 75.3 kDa on reducing gels. Yet another preferred embodiment of the invention features a sciellin which is reactive with a sciellin-specific antibody, e.g., an antibody which binds to the epitope recognized by mAb 34D11, or a polyclonal antibody SC4. Antibodies against sciellin can be made by methods exemplified herein.

In another preferred embodiment, sciellin is expressed by a recombinant cell, e.g., a bacterial cell, a cultured cell (e.g., a cultured eukaryotic cell) or a cell of a non-human transgenic animal. Cultured cells can include CHO cells or SF8 cells. Expression of sciellin in a transgenic animal can be general or can be under the control of a tissue specific promoter. Preferably, one or more sequences which encode sciellin or a fragment thereof are expressed in a preferred cell-type by a tissue specific prtomoter, e.g., a K14 promoter. Exemplary sequences encoding fragments of sciellin include, e.g., a sequence encoding the central domain of sciellin, e.g., one or more of repeats 1–16, or a sequence encoding a LIM domain.

In a preferred embodiment, the recombinant sciellin differs from sciellen isolated from tissue in one or more of the following: its pattern of glycosylation, myristilation, phosphorylation, or other posttranslational modifications.

In a preferred embodiment, the recombinant sciellin preparation is free of other keratinocyte proteins, placental proteins, or other human proteins.

In a preferred embodiment, the recombinant sciellin preparation contains at least 1, 10, or 100 µg of sciellin, or a sciellin polypeptide.

In a preferred embodiment, the recombinant sciellin preparation contains at least 1, 10, or 100 mg of sciellin, or a sciellin polypeptide.

In a preferred embodiment, the sciellin polypeptide has the following biological acitivities: 1) it is a precursor of the cornified envelopelof keratinizing tissues; 2) it provides structural support to the comified envelopes of stratum corneum cells; 3) it promotes adhesion between tissue elements; 4) it promotes intracIellular signalling; 5) it defines cell shape; 6) it can act as an adaptor element to promote the assembly and targeting of multiprotein complexes; 7) it forms homotrimeric beta helices; (8) it is involved in the terminal differentiation of keratinocytes; and (9) it plays a role in development. In other preferred embodiments: the sciellin polypeptide includes an amino acid sequence with at least 60%, 80%, 90%, 95%, 98%, or 99% sequence identity to an amino acid sequence from SEQ ID NO:2; the sciellin polypeptide includes an amino acid sequence essentially the same as the amino acid sequence in SEQ ID NO:2; the sciellin polypeptide is at least 5, 10, 20, 50, 100, or 150 amino acids in length; the sciellin polypeptide includes at least 5, preferably at least 10, more preferably at least 20, most preferably at least 50, 100, or 150 contiguous amino acids from SEQ ID NO:2; the sciellin polypeptide is either, an agonist or an antagonist, of a biological activity of naturally occurring sciellin; the sciellin polypeptide is a vertebrate, e.g., a mammalian, e.g. a primate, e.g., a human, sciellin polypeptide.

In preferred embodiments: the sciellin polypeptide is encoded by the nucleic acid in SEQ ID NO:1, or by a nucleic acid having at least about1 85%, more preferably at least about 90% to about 95%, and most preferably at least about 99% sequence identity with the nucleic acid from SEQ ID NO:1.

In preferred embodiments, the sciellin polypeptide includes an amino terminal domain, a central domain containing comprised of sixteen repeats, and/or a carboxy terminal domain containing a LIM domain.

In preferred embodiments, the sciellin polypeptide includes a domain that includes at least one repeat, preferably 10 to 20 repeats, more preferably 14 to 18 repeats, and most preferably about 16 repeats. Generally, the domain is about 20 residues in length, and preferably, has about 70, 80, 90, or 95% sequence identity with the protein sequence shown in SEQ ID NO:2 (amino acid residues 231–543). Preferably, each repeat includes alternating stretches of hydrophobicity and hydrophilicity on hydropathy plots. Preferred hydrophobic stretches are about 3 to 10, preferably 4 to 9, most preferably, 5 to 7 residues in length. In one embodiment, the hydrophobic stretches can form beta sheets. In yet another embodiment, the invention features a sciellin polypeptide that does not include or has an inactivation in at least one repeat, preferably 10 to 20 repeats, more preferably 14 to 18 repeats, and most preferably about 16 repeats, which serves as an antagonist to one or more sciellin biological activities.

In preferred embodiments, the sciellin polypeptlide includes a LIM domain. Generally, the LIM domain is about 56 amino acids, and preferably has about 70, 80, 90, or 95% sequence identity with the protein sequence shown in SEQ ID NO:2 (amino acid residues 600–662). Preferably, the LIM domain folds in to two independent structural domains with at least one cysteine and at least one histidine residues coordinating two zinc ions. In one embodiment, the LIM domain includes at least 5, preferably 6 to 7, and most preferably 8 of the cysteins and up to 3, most preferably one histidine found in native sciellin. In one embodiment, the LIM domain has a consensus sequence $CX_2CX_{16-23}HX_2CX_2CX_2CX_{16-21}CX_{2-3}(C,H,D)$, wherein X can be any amino acid.

In a preferred embodiment, the sciellin polypeptide differs in amino acid sequence at up to 1, 2, 3, 5, or 10 residues, from a sequence in SEQ ID NO:2. In other preferred embodiments, the sciellin polypeptide differs in amino acid sequence at up to 1, 2, 3, 5, or 10% of the residues from a sequence in SEQ ID NO:2. Preferably, the differences are such that: the sciellin polypeptide exhibits a sciellin biological activity, e.g., the sciellin polypeptide retains a biological activity of a naturally occurring sciellin.

In preferred embodiments the sciellin polypeptide includes a sciellin sequence described herein as well as other N-terminal, and/or a C-terminal amino acid sequence.

In preferred embodiments, the sciellin polypeptide includes all or a fragment of an amino acid sequence from SEQ ID NO:2, fused, in reading frame, to additional amino acid residues, preferably to residues encoded by genomic DNA 5' to the genomic DNA which encodes a sequence from SEQ ID NO:2.

In yet other preferred embodiments, the sciellin, polypeptide is a recombinant fusion protein having a first sciellin portion and a second pol eptide portion, e.g., a second polypeptide portion having an amino acid sequence unrelated to sciellin. The second polypeptide portion can be, e.g., any of glutathione-S-transferase, a DNA binding domain, or a polymerase activating domain. In a preferred embodiment the fusion protein can be used in a two-hybrid assay. For example, a first sciellin portion, e.g., a sciellin portion containing a LIM domain, e.g., amino acids 550 to end encoded by the last exon, can be fused to a DNA binding domain. In a two hybrid assay, the first sciellin portion is co-expressed in a cell with a second polypeptide portion containing a transcription activation domain fused to an expression library, e.g., a keratinocyte library.

In a preferred embodiment the sciellin polypeptide includes amino acid residues 231–543 of SEQ ID NO:2 In another embodiment, the sciellin polypeptide includes amino acids 600–662 of SEQ ID NO:2.

In preferred embodiments the sciellin polypeptilde has antagonistic activity, and is capable of: inhibiting formation of the cornified envelope in keratinizing tissues.

In a preferred embodiment, the sciellin polypeptide is a fragment of a naturally occurring sciellin which inhibits formation of the cornified envelope in keratinizing tissues.

Polypeptides of the invention include those which arise as a result of the existence of multiple genes, alternative transcription events, alternative RNA splicing events, and alternative translational and postranslational events. The sciellin polypeptide can be expressed in systems, e.g., cultured cells, which result in substantially the same postranslational modifications present when expressed sciellin is expressed in a native cell, or in systems which result in the omission of postranslational modifications present when expressed in a native cell.

The invention includes an immunogen which includes a sciellin polypeptide in an immunogenic preparation, the immunogen being capable of eliciting an immune response specific for the sciellin polypeptide, e.g., a humoral response, an antibody response, or a cellular response. In preferred embodiments, the immunogen comprising an antigenic determinant, e.g., a unique determinant, from a protein represented by SEQ ID NO:2.

The present invention also includes an antibody preparation specifically reactive with an epitope of the sciellin immunogen or generally of a sciellin polypeptide, preferably an epitope which consists all or in part of residues from the the amino acid sequence of SEQ ID NO:2, or an epitope, which when bound to an antibody, results in the modulation of a biological activity.

In preferred embodiments the sciellin-like polypeptide, as expressed in the cells in which it is normally expressed or in other eukaryotic cells, has a molecular weight of about 75.3 kDa as determined by SDS-PAGE.

In another embodiment, the sciellin polypeptide comprises amino acid residues 1–668 of FIG. 2 (SEQ ID NO:2).

In a preferred embodiment, the recombinant sciellin polypeptide has one or more of the following characteristics:

(i) it has the ability to form homotrimerilc beta helices;

(ii) it acts as a precursor of the cornified envelope of keratinizing tissues;

(iii) it provides structural support to the cornified envelopes of stratum corneum cells;

(iv) it promotes adhesion between tissue elements;

(v) it promotes intracellular signalling;

(vi) it defines cell shape;

(vii) it can act as an adaptor element to promote the assembly and targeting of multiprotein complexes;

(viii) it has a molecular weight, amino acid composition or other physical characteristic of sciellin of SEQ ID NO:2;

(ix) it has an overall sequence similarity of at least 50%, preferably at least 60%, more preferably at least 70, 80, 90, or 95%, with a sciellin polypeptide of SEQ ID NO:2;

(x) it is found in human placenta;

(xi) it has a central domain composed of repeats which is preferably about 70%, 80%, 90% or 95% identical to amino acid residues 231–543 of SEQ ID NO:2;

(xii) it has a carboxyl domain containing a single LIM domain which is preferably about 70%, 80%, 90% or 95% identical to amino acid residues 600–662 of SEQ ID NO:2;

(xiii) it has a pI of about 10;

(xiv) it can be expressed in the stratum granulosum of human foreskin tissue; and (xv) it can expressed in the peripheral cytoplasm in hair follicles, upper cell layer of epidermis, as well as the epithelium of the orali cavity, esophagus, vagina, ureter and cornea.

Also included in the invention is a composition which includes a sciellin polypeptide (or a nucleic acid which encodes it) and one or more additional components, e.g., a carrier, diluent, or solvent. The additional component can be one which renders the composition useful for in vitro and in vivo pharmaceutical or veterinary use.

In another aspect, the invention provides an isolated or substantially pure nucleic acid having or comprising a nucleotide sequence which encodes a sciellin or a sciellin polypeptide, e.g., a sciellin or a sciellin polypeptide described herein.

A preferred embodiment of the invention features a nucleic acid molecule having a nucleotide sequence at least about 85% sequence identity to a nucleotide sequence of SEQ ID NO:1. In other preferred embodiments, the sciellin polypeptide is encoded by a nucleic acid molecule having a nucleotide sequence with at least about 90% to about 95%, and more preferably about 98% to about 99% sequence identity to the nucleotide sequence from SEQ ID NO:1. In another preferred embodiment, the sciellin polypeptide is encoded by the nulceic acid molecule of SEQ ID NO:1.

In preferred embodiments, the subject sciellin nucleic acid will include a transcriptional regulatory sequence, e.g. at least one of a transcriptional promoter or transcriptional enhancer sequence, operably linked to the sciellin gene sequence (also referred to as LAMG3), e.g., to render the sciellin gene sequence suitable for use as an expression vector.

In yet a further preferred embodiment, the nucleic acid which encodes a sciellin polypeptide of the invention, hybridizes under stringent conditions to a nucleic acid probe corresponding to at least 12 consecutive nucleotides ofiSEQ ID NO:1. More preferably, the nucleic acid probe corresponds to at least 20 consecutive nucleotides from SEQ ID NO:1.

The invention also provides a probe or primer which includes or comprises a substantially purified oligonucleotide. The oligonucleotide includes a region of nucleotide sequence which hybridizes under stringent conditions to at least 10 consecutive nucleotides of sense or antisense sequence from SEQ ID NO:1, or naturally occurring mutants thereof. In preferred embodiments, the probe or primer further includes a label group attached thereto. The label group can be, e.g., a radioisotope, a fluorescen t compound, an enzyme, and/or an enzyme co-factor. Preferably the oligonucleotide is at least 10 and less than 20, 30, 50, 100, or 150 nucleotides in length.

The invention involves nucleic acids, e.g., RNA or DNA, encoding a sciellin polypeptide of the invention. This includes double stranded nucleic acids as well as coding and antisense single strands.

In another aspect, the invention features a cell or purified preparation of cells which include a sciellin transgene, or which otherwise misexpress a sciellin gene. The cell preparation can consist of human or non human cells, e.g., rodent cells, e.g., mouse or rat cells, rabbit cells, or pig cells. In preferred embodiments, the cell or cells include a sciellin transgene, e.g., a heterologous form of a sciellin gene, e.g., a gene derived from humans (in the case of a non-human cell). The sciellin transgene can be misexpressed, e.g., overexpressed or underexpressed. In other preferred embodiments, the cell or cells include a gene which misexpress an endogenous sciellin gene, e.g., a gene the expression of which is disrupted, e.g., a knockout. Such cells can serve as a model for studying disorders which are related to mutated or mis-expressed sciellin alleles or for use in drug screening.

In another aspect, the invention features a transgenic sciellin animal, e.g., a rodent, e.g., a mouse or a rat, a rabbit, a pig, a goat, or a cow. In preferred embodiments, the transgenic animal includes (and preferably express) a heterologous form of a sciellin gene, e.g., a gene derived from humans. In a further embodiment, the sciellin transgene includes a tissue specific promoter, e.g., a K14 promoter. In other preferred embodiments, the animal has an endogenous sciellin gene which is misexpressed, e.g., a knockout. Such a transgenic animal can serve as a model for studying disorders which are related to mutated or mis-expressed sciellin alleles or for use in drug screening.

In another aspect, the invention features, a method of inducing differentiation of keratinocytes. The method includes contacting a keratiniocyte with an amount of a sciellin molecule described herein, or a sciellin agent, sufficientito induce differentiation. The sciellin agent can be an agonist or an antagonist of sciellin activity. The method can be performed in vivo, or in vitro. In in vivo methods the sciellin is administered to the subject. The administration can be directed to the site where differentiation is desired, e.g., by topical application or by injection, or administered in a systemic fashion.

In another aspect, the invention features, a method of promoting hair growth. The method includes contacting a hair stem cells with an amount of a sciellin molecule described herein or a sciellin agent, sufficient to induce hair growth. The sciellin agent can be an agonist or an antagonist of sciellin activity. The method can be performed in vivo, or in vitro. In in vivo methods the sciellin is administered to the subject. The administration can be directed to the site where hair growth is desired, e.g., by topical application or by injection, or administered in a systemic fashion.

In another aspect, the invention features, a method of promoting adhesion of a first tissue element to a second tissue element. The method includes contacting one or both of the first tissue element and the second tissue element with an amount of a sciellin molecule described herein or a sciellin agent, sufficient to promote adhesion. The sciellin agent can be an agonist or an antagonist of sciellin activity. The method can be performed in vivo, or in vitro. In in vivo methods the sciellin is administered to the subject. The administration can be directed to the site where adhesion is desired, e.g., by topical application or by injection, or administered in a systemic fashion.

A tissue element can be a cell or a multi-cellularion acellular structure. Examples of tissue elements include, skin cells, e.g., epidermal or dermal cells, or e.g., foreskin tissue, e.g., stratum granulosum, basement membrane or components of the basement membrane, hair follicles, epithelium in the oral cavity, esophagus, vagina, ureter and cornea, or any cell or structure which in normal, non-traumatized, or non-diseased tissue is adjacent or adhered to a specific tissue element recited herein.

In preferred embodiments the molecule is exogenous (e.g., administered to a subject) or is recombinant.

In preferred embodiments the method is an vivo method. In vivo methods can be autologous, allogeneic, or xenogeneic. In autologous methods, adhesion between two tissue elements from the subject is promoted. In allogeneic methods, adhesion between a recipient tissue element and a donor tissue element from an allogeneic donor is promoted. In xenogeneic methods, adhesion between a recipient tissue element and a donor tissue element from a xenogeneic donor is promoted. Thus, one element can be a donor tissue element which is implanted into a recipient subject.

In preferred embodiments the first tissue is healthy tissue, e.g., skin tissue, and the second tissue is wounded, e.g., burned, diseased, traumatized, cut, and the tissue, or is a wound bed. For example, the first tissue is skin tissue, from the subject or from a donor, and the second tissue is wounded, e.g., burned or abraided tissue.

In preferred embodiments the first tissue and second tissue element are normally adhered but have become detached from one another due to trauma, burn or other physical injury, disease, or age.

In preferred embodiments: the first tissue element is a dermal cell and the second tissue element is an epidermal cell; the first tissue element is e.g., foreskin tissue, e.g., stratum granulosum, hair follicles, part of the epithelium in the oral cavity, esophagus, vagina, ureter and cornea and the second tissue element is a cell or structure which in normal, non-traumatized, or non-diseased tissue is adjacent or adhered to said epithelium.

The administration of sciellin can be repeated.

In another aspect, the invention features a method of promoting wound healing in a subject. The method includes administering an amount of a sciellin molecule described herein or a sciellin agent, sufficient to promote healing to the wound. The sciellin agent can be an agonist or an antagonist of sciellin activity. The administration can be directed to the site where healing is desired, e.g., by topical application or by injection, or administered in a systemic fashion.

The wound can be in any tissue, but preferably in a tissue in which the sciellin normally occurs. Examples skin, e.g., foreskin tissue, e.g., stratum granulosum, hair follicles, tissues of the eye, e.g., the cornea, the basement membrane the epithelium in, e.g., the oral cavity, esophagus, vagina, ureter, or any tissue which in normal, non-traumatized, or non-diseased tissue is adjacent or adhered thereto.

In preferred embodiments the molecule is exogenous (e.g., administered to a subject) or is recombinant.

In preferred embodiments the wound tissue is burned, diseased, traumatized, cut, the subject of immune attack, e.g., autoimmune attack, or abraided.

The administration of sciellin can be repeated.

In another aspect, the invention provides, a method of treating or preventing in a subject a sciellin- related disorder. The method includes: administering to the subject an effective amount of sciellin molecule, or a sciellin agonist, effective to treat or prevent the sciellin- related disorder in the subject. The sciellin agent can be an agonist or an antagonist of sciellin activity. The administration can be directed to the site where treatment or prevention is desired, e.g., by topical application or by injection, or administered in a systemic fashion.

In preferred embodiments, the subject is a mammal, e.g., human or non-human.

Such sciellin-related disorders include, e.g., a disorder associated with the misexpression of sciellin; a skin disorder, e.g., a foreskin disorder; an epidermal disorder, e.g., a disorder characterized by disturbed epidermal characterization or a disorder in the stratum granulosum, e.g., ichthyosis; an ectodermal disorder, e.g., ectodermal dysplasia; a dermal disorder; a hair growth disorder, e.g., congenital allopecia; a disorder associated with a genetic lesion at chromosome 13, region q22; a disorder associated with abnormal levels, e.g., abnormally low levels, of adhesion between tissues; a disorder associated with the basement membrane; a disorder associated with abnormal keratinocyte activity; e.g., abnormal activity of keratinocytes in the epithelium of oral cavity, esophagus, vagina, ureter or cornea; or an inflammatory condition.

In preferred embodiments the molecule is exogenous (e.g., administered to a subject) or is recombinant.

The administration of sciellin can be repeated.

In another aspect, the invention provides, a method of determining if a subject is at risk for a disorder related to a lesion in or the misexpression of a gene which encodes a sciellin described herein.

Such disorders include, e.g., a disorder associated with the misexpression of sciellin; a skin disorder, e.g., a foreskin disorder; an epidermal disorder, e.g., a disorder characterized by disturbed epidermal characterization or a disorder in the stratum granulosum, e.g., ichthyosis; an ectodermal disorder, e.g., ectodermal dysplasia; a dermal disorder; a hair growth disorder, e.g., congenital allopecia; a disorder associated with a genetic lesion at chromosome 13, region q22; a disorder associated with abnormal levels, e.g., abnormally low levels, of adhesion between tissues; a disorder associated with the basement membrane; a disorder associated with abnormal keratinocyte activity; e.g., abnormal activity of keratinocytes in the epithelium of oral cavity, esophagus, vagina, ureter or cornea; or an inflammatory condition.

The method includes one or more of the following:

detecting, in a tissue of the subject, the presencelor absence of a mutation which affects the expression of the sciellin gene, or other gene which encodes a subunit of sciellin, e.g., detecting the presence or absence of a mutation in a region which controls the expression of the gene, e.g., a mutation in the 5' control region;

detecting, in a tissue of the subject, the presence or absence of a mutation which alters the structure of the sciellin gene;

detecting, in a tissue of the subject, the misexpression of the sciellin gene, at the mRNA level, e.g., detecting a non-wild type level of a sciellin mRNA;

detecting, in a tissue of the subject, the misexpression of the sciellin gene, at the protein level, e.g., detecting a non-wild type level of a sciellin polypeptide.

In preferred embodiments the method includes: ascertaining the existence of at least one of: a deletion of one or more nucleotides from the sciellin gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1, or naturally occurring mutants thereof or 5' or 3' flanking sequences naturally associated with the LAMG3 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the sciellin gene; the presence of a non-wild type splicing pattern of a messenger RNA transcript of the sciellin gene; or a non-wild type level of sciellin.

Methods of the invention can be used prenatally or to determine if a subject's offspring will be at risk for a disorder.

In preferred embodiments the method includes determining the structure of a sciellin gene, an abnormal structure being indicative of risk for the disorder.

In preferred embodiments the method includes contacting a sample form the subject with an antibody to the sciellin protein or a nucleic acid which hybridizes specifically with the sciellin gene,.

In another aspect, the invention features, a method of evaluating a compound for the ability to interact with, e.g., bind, a subject sciellin polypeptide, e.g., sciellin or a fragment thereof, e.g., a central repeat domain, or a LIM domain, of sciellin. The method includes: contacting the compound with the subject sciellin polypeptide; and evaluating ability of the compound to interact with, e.g., to bind or form a complex with the subject sciellin polypeptide. This method can be performed in vitro, e.g., in a cell free system, or in vivo, e.g., in a two-hybrid interaction trap assay. This method can be used to identify naturally occurring molecules which interact with subject sciellin polypeptide. It can also be used to find natural or synthetic inhibitors of subject sciellin polypeptide.

In another aspect, the invention features, a method of evaluating a compound, e.g., a polypeptide, e.g., a naturally occurring ligand of or a naturally occuring substrate to which binds a subject sciellin polypeptide, e.g., sciellin or a fragment thereof, e.g., a central repeat domain, or a LIM domain, of sciellin, for the ability to bind a subject sciellin polypeptide. The method includes: contacting the compound with the subject sciellin polypeptide; and evaluating the ability of the compound to interact with, e.g., to bind or form a complex with the subject sciellin polypeptide, e.g., the ability of the compound to inhibit a subject sciellin polypeptide/ligand interaction. This method can be performed in vitro, e.g., in a cell free system, or in vivo, e.g., in a two-hybrid interaction trap assay. This method can be used to identify compounds, e.g., fragments or analogs of a subject sciellin polypeptide, which are agonists or antagonists of a subject sciellin polypeptide.

In another aspect, the invention features, a method of evaluating a first compound, e.g., a subject sciellin polypeptide, e.g., sciellin or a fragment thereof, e.g., a central repeat domain, or a LIM domain, of sciellin, for the ability to bind a second compound, e.g., a second polypeptide, e.g., a naturally occurring ligand of or substrate to which binds a subject sciellin polypeptide. The method includes: contacting the first compound with the second compound; and evaluating the ability of the first compound to form a complex with the second compound. This method can be performed in vitro, e.g., in a cell free system, or in vivo, e.g., in a two-hybrid interaction trap assay. This method can be used to identify compounds, e.g., fragments or analogs of a subject sciellin polypeptide, which are agonists or antagonists of a subject sciellin polypeptide.

In yet another aspect, the invention features a method for evaluating a compound, e.g., for the ability to modulate an interaction, e.g., the ability to inhibit an interaction of a subject sciellin polypeptide, e.g., sciellin or a fragment thereof, e.g., a central repeat domain, or a LIM domain, of sciellin, with a second polypeptide, e.g., a polypeptide, e.g., a natural ligand of the of or a substrate wo which binds a subject sciellin polypeptide, or a fragment thereof. The method includes the steps of (i) combining the second polypeptide (or preferably a purified preparation thereof), a subject sciellin polypepltide, (or preferably a purified preparation thereof), and a compound, e.g., under conditions wherein in the absence of the compound, the second polypeptide, and the subject sciellin polypeptide, are able to interact, e.g., to bind or form a complex; and (ii) detecting the interaction, e.g., detecting the formation (or dissolution) of a complex which includes the second polypeptide, and the subject sciellin polypeptide. A change, e.g., a decrease or increase, in the formation of the complex in the presence of a compound (relative to what is seen in the absence of the compound) is indicative of a modulation, e.g., an inhibition or promotion, of the interaction between the second polypeptide, and the subject sciellin polypeptide. In preferred embodiments: the second polypeptide, and the subject sciellin polypeptide, are combined in a cell-free system and contacted with the compound; the cell-free system is selected from a group consisting of a cell lysate and a reconstituted protein mixture; the subject sciellin polypeptide, and the second polypeptide are simultaneously expressed in a cell, and the cell is contacted with the compound, e.g. in an interaction trap assay (e.g., a two-hybrid assay).

In yet another aspect, the invention features a two-phase method (e.g., a method having an in vitro, e.g., in a cell free system, and an in vivo phase) for evaluating a compound, e.g., for the ability to modulate, e.g., to inhibit or promote, an interaction of a subject sciellin polypeptide subject sciellin polypeptide ,e.g., sciellin or a fragment thereof, e.g., a central repeat domain, or a LIM domain, of sciellin, with a second compound, e.g., a second polypeptide, e.g., a naturally occurring ligand of or a substrate to which binds a subject sciellin polypeptide, or a fragment thereof. The method includes steps (i) and (ii) of the method described immediately above performed in vitro, and further includes: (iii) determining if the compound modulates the interaction in vitro, e.g., in a cell free system, and if so; (iv) administering the compound to a cell or animal; and (v) evaluating the in vivo effect of the compound on an interaction, e.g., inhibition, of a subject sciellin polypeptide, with a second polypeptide.

In another aspect, the invention features, a method of evaluating a compound for the ability to bind a nucleic acid encoding a subject sciellin polypeptide, e.g., sciellin or a fragment thereof, e.g., a central repeat domain or a LIM domain. The method includes: contacting the compound with the nucleic acid; and evaluating ability of the compound to form a complex with the nucleic acid.

In another aspect, the invention features a method of making a sciellin polypeptide, e.g., a peptide having a non-wild type activity, e.g., an antagonist, agonist, or super agonist of a naturally occurring sciellin polypeptide, e.g., a naturally occurring sciellin polypeptide. The method includes: altering the sequence of a sciellin polypeptide, e.g., altering the sequence , e.g., by substitution or deletion of one or more residues of a non-conserved region, a domain or residue disclosed herein, and testing the altered polypeptide for the desired activity.

In another aspect, the invention features a method of making a fragment or analog of a sciellin polypeptide having a biological activity of a naturally occurring sciellin polypeptide. The method includes: altering the sequence, e.g., by substitution or deletion of one or more residues, of a sciellin polypeptide, e.g., altering the sequence of a non-conserved region, or a domain or residue described herein, and testing the altered polypeptide for the desired activity.

In another aspect, the invention features, a human cell, e.g., a skin cell, e.g., an epithelial cell, e.g., a keratinocyte, transformed with nucleic acid which encodes a subject sciellin polypeptide.

In another aspect, the invention includes: a sciellin nucleic acid, e.g., a sciellin nucleic acid inserted into a vector; a cell transformed with a sciellin nucleic acid; a sciellin made by culturing a cell transformed with a sciellin nucleic acid; and a method of making a sciellin polypeptide including culturing a cell transformed with a sciellin nucleic acid.

A "heterologous promoter", as used herein is a promoter which is not naturally associated with a gene or a purified nucleic acid.

A "purified" or "substantially pure" or isolated "preparation" of a polypeptide, as used herein, means a polypeptide that has been separated from other proteins, lipids, and nucleic acids with which it naturally occurs. Preferably, the polypeptide is also separated from substances, e.g., antibodies or gel matrix, e.g., polyacrylamide, which are used to purify it. Preferably, the polypeptide constitutes at least 10, 20, 5p 70, 80 or 95% dry weight of the purified preparation. Preferably, the preparation contains: sufficient polypeptide to allow protein sequencing; at least 1, 10, or 100 $\mu$g of the polypeptide; at least 1, 10, or 100 mg of the polypeptide.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

A "treatment", as used herein, includes any therapeutic treatment, e.g., the administration of a therapeutic agent or substance, e.g., a drug.

As used herein, the term "subject" refers to human and non-human animals. In preferred embodiments, the subject is a human, e.g., person, e.g., a person having a sciellin related disorder. The term "non-human animals" of the, invention includes all vertebrates, e.g., mammals and non-mammals, such as non-human primates, ruminants, birds, amphibians, reptiles.

An "isolated" or "pure nucleic acid", e.g., a substantially pure DNA, is a nucleic acid which is one or both of: not immediately contiguous with either one or both of the sequences, e.g., coding sequences, with which it is immediately contiguous (i.e., one at the 5' end and one at the 3' end) in the naturally-occurring genome of the organism from which the nucleic acid is derived; or which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA can also includes a recombinant DNA which is part of a hybrid gene encoding sequence.

"Sequence identity or homology", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the sequences divided by the number of positions compared× 100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithim. Preferably, the alignment can be performed using the Clustal Method. Multiple alignment paramethers include GAP Penalty=10, Gap Length Pehalty=10. For DNA alignments, the pairwise alignment paramenters can beg Htuple=2, Gap penalty=5, Window=4, and Diagonal saved=4. For protein alignments, the pairwise alignment parameters can be Ktuple=1, Gap penalty=3, Window=5, and Diagonals Saved=5.

Additional non-limiting example of a mathematical algorithim utilized for the comparison of sequences is the algorithm of Karlin and Altschul (1990) Proc. Natl. Acad. Sci. USA 87:2264–68, modified as in Karlin and Altschul (1993) Proc. Natl. Acad. Sci. USA 90:5873–77. Such an algorithm is incorporated into the NBLAST and XBLAST programs (version 2.0) of Altschul, et al. (1990) J. Mol. Biol. 215:403–10. BLAST nucleotide searches can be performed performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Research 25(17):3389–3402. When utilizing BLAST and Gapped BLAST programs, the default parameters of the respective programs (e.g., XBLAST and NBLAST) can be used. See http://www ncbi.nlm.nih.gov. Another preferred, non-limiting example of a mathematical algorithim utilized for the comparison of sequences is the algorithm of Myers and Miller, CABIOS (1 989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The terms "peptides", "proteins", and "polypeptides" are used interchangeably herein.

As used herein, the term "transgene" means a nucleic acid sequence (encoding, e.g., one or more subject sciellin polypeptides), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of the selected nucleic acid, all operably linked to the selected nucleic acid, and may include an enhancer sequence.

As used herein, the term "transgenic cell" refersito a cell containing a transgene.

As used herein, a "transgenic animal" is any animal in which one or more, and preferably essentially all, of the cells of the animal includes a transgene. The transgene can be introduced into the cell, directly or indirectly by introduction into a precursor of the cell, by way of deliberate genetic manipulation, such as by microinjection or by infection with a recombinant virus. This molecule may be integrated within a chromosome, or it may be extrachromosomally replicating DNA.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as mammary tissue. The term also covers so-called "leaky" promoters, which regulate expression of a selected DNA primarily in one tissue, but cause expression in other tissues as well.

"Unrelated to a sciellin amino acid or nucleic acid sequence" means having less than 30% sequence identity, less than 20% sequence identity, or, preferably, less than 10% homology with a naturally occuring sciellin sequence disclosed herein.

A polypeptide has sciellin biological activity if it has one or more of the properties of sciellin disclosed herein. A polypeptide has biological activity if it is an antagonist, agonist, or super-agonist of a polypeptide having one of the properties of sciellin disclosed herein.

"Misexpression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

Subject, as used herein, can refer to a mammal, e.g., a human, or to an experimental or animal or disease model. The subject can also be a non-human animal, e.g., a horse, cow, goat, or other domestic animal.

As described herein, one aspect of the invention features a substantially pure (or recombinant) nucleic acid which includes a nucleotide sequence encoding a sciellin polypeptide and/or equivalents of such nucleic acids. The term nucleic acid as used herein can include fragments and equivalents. The term equivalent refers to nucleotide sequences encoding functionally equivalent polypeptides. Equivalent nucleotide sequences will include sequences that differ by one or more nucleotide substitutions, additions or deletions, such as allelic variants, and include sequences that differ from the nucleotide sequences disclosed herein by degeneracy of the genetic code.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning, Volumes I and II* (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology, Volumes I–IV* (D. M. Weir and C. C. Blackwell, eds., 1986); *Manipulating the Mouse Embryo*, (Cold Spring Harbor Laboratory Press, Cold Spring Harbor, N.Y., 1986).

High stringency aqueous hybridization of nucleic acids can be conducted at 68° C., in 6X SSC, 0.5% SDS, followed by a wash in 2X SSC, 0.1% SDS at room temperature; a wash in 0.1X SSC, 0.5% SDS at 37° C.; and a final wash in 0.1 X SSC, 0.5% SDS at 68° C. (Molecular Cloning, A Laboratory Manual, 2d Ed., ed. by Sambrook, Fritsch and Maniatis, Cold Spring Harbor Laboratory Press, 1989, 9.52–9.55).

Other features and advantages of the inventions will be apparent from the following detailed description, and from the claims.

DETAILED DESCRIPTION

The drawings are briefly described.

FIG. 2 depicts the nucleotide sequence of sciellin cDNA and its predicted amino acid sequence.

FIG. 3 depicts the predicted sciellin amino acid sequence (SEQ ID NO:2). Sixteen (16) repeats of approximately twenty (20) residues are found from residue 231–543. A single LIM domain of approximately fifty-six (56)m amino acids is located from residue 600–662. The sequences obtained from tryptic peptides are underlined, and cysteine residues are circled.

Figure 4:
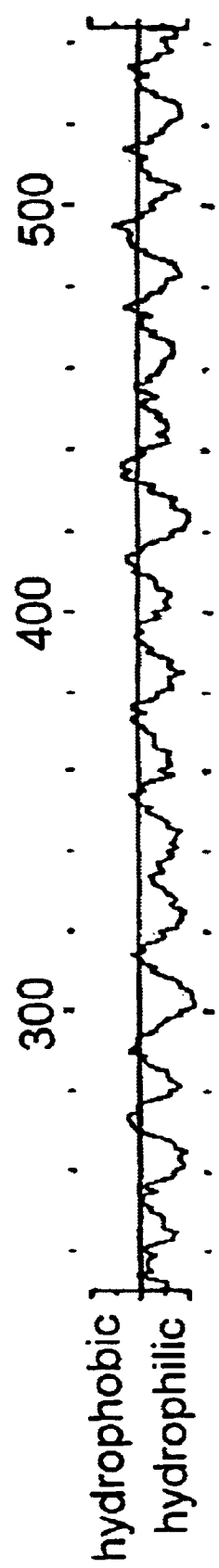

FIG. 4 depicts a hydropathy plot of all sixteen sciellin repeats from residue 231 to 543. The sciellin repeats are characterized by alternating hydrophobic and hydrophilic regions.

FIG. 5 depicts an alignment of sciellin LIM domain with several other LIM proteins. The consensus Cys and His residues are boxed. The relative positions of the LIM domains are indicated. The sequences are numbered from 1 to 8 as follows: 1 - sciellin [*Homo sapiens*] (SEQ ID NO:3) (Genbank Accession Number: AF045941), 2 - LIM-domain protein [*Homo sapiens*] (SEQ ID NO:4) (Genbank Accession Number: Y09538), 3 - P1-A [*Mus musculus*] (SEQ ID NO:5) (Genbank Accession Number: U46687), 4 - zinc-finger domain-containing protein [*Homo sapiens*] (SEQ ID NO:6) (Genbank Accession Number: U90654), 5 - F28F5.2 gene product [*C. elegans*] (SEQ ID NO:7) (Genbank Accession Number: U00045), 6 - skeletal muscle LIM-protein FHL1 [*Homo sapiens*] (SEQ ID NO:8) (Genbank Accession Number: U60115), 7 - zyxin [*Mus musculus*] (SEQ ID NO:9) (Genbank Accession Number: Y07711), 8 - zyxin 2 [*Homo sapiens*] (SEQ ID NO:10) (Genbank Accession Number: X94991).

Figure 6:
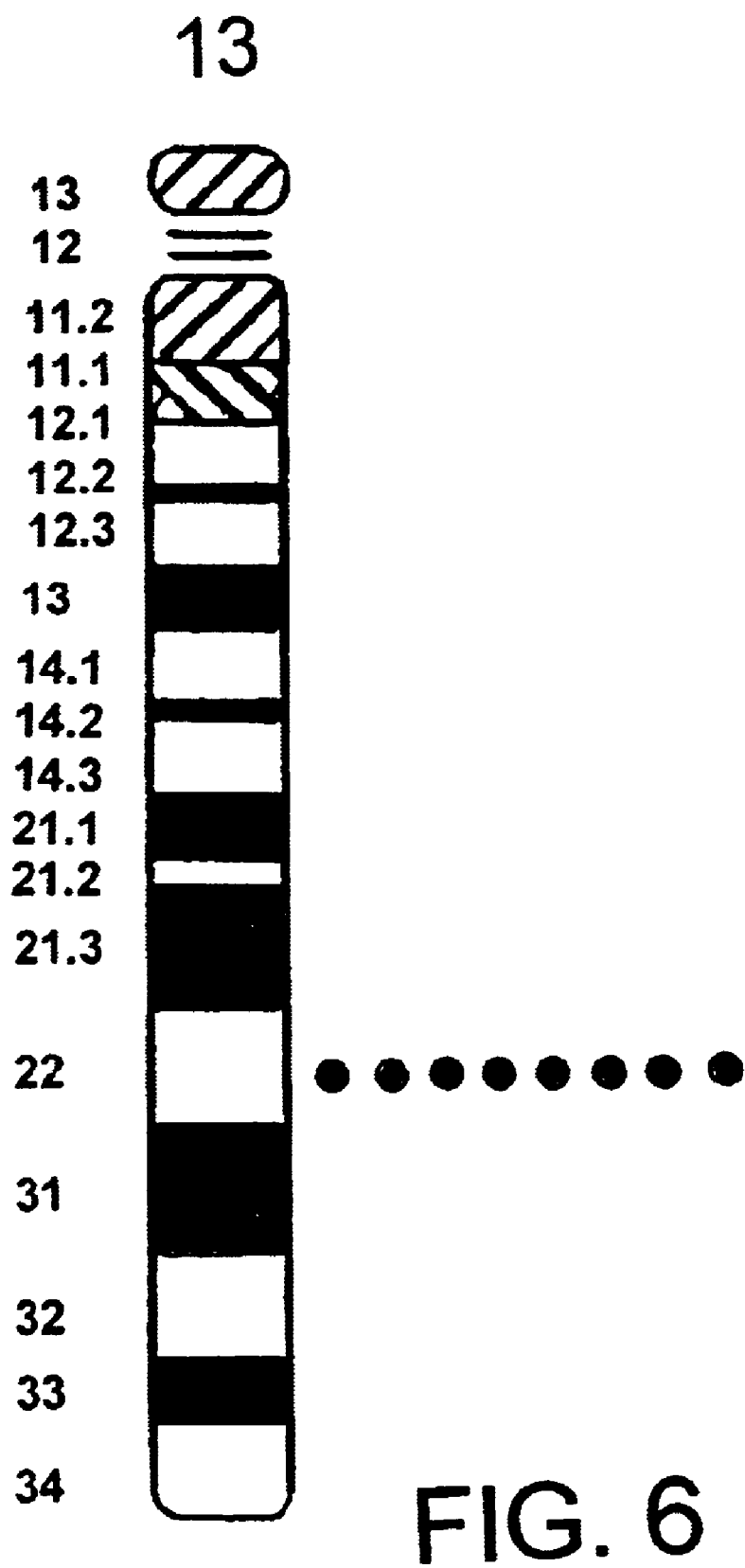

FIG. 6 depicts the results of chromosomal mapping of the sciellin gene to chromosome 13, band q22.

ISOLATION AND CLONING OF SCIELLIN CDNA

Figure 1:
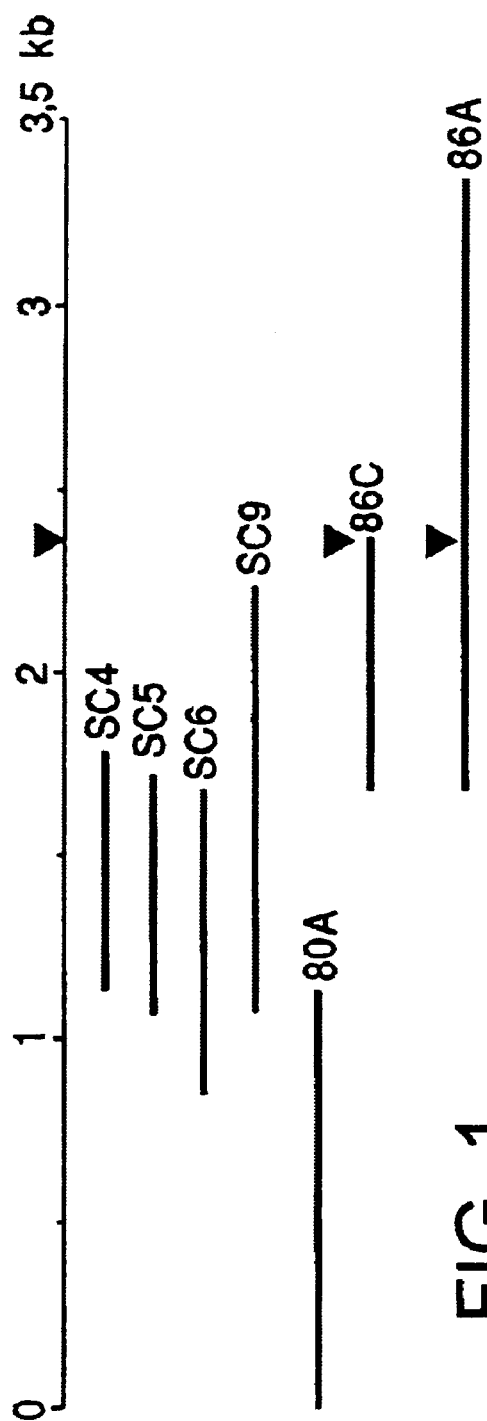
FIG. 1 depicts a map of overlapping sciellin cDNA clones. The positions of the polyadenylation signals and poly(A)+ tails are indicated by arrowheads.

A human foreskin keratinocyte library packaged in lambda gt11 (Gerecke, D. R. et al. (1994) *J. Biol. Chem.* 269:11073–11080) was screened with a 1:50 dilution of the monoclonal Ab 34D11 specific for the cornified envelope precursor sciellin (Baden, H. P. et al. (1987) *J. Invest. Dermatol.* 89:454–459). Detection was performed using a 1:500 dilution of goat anti-mouse HRP secondary antibody (I.C.N.) and chloronapthol (Biorad) according to standard protocols (Sambrook, J. et al. (1989) *Molecular Cloning: A Laboratory Manual*, 2nd Ed., Cold Spring Harbor Laboratory, Cold Spring Harbor, NY). Duplicating positive clones were analyzed by DNA sequencing and Northern blotting. FIG. 1 is a graphic representation of overlapping sciellin cDNA clones. Four positive clones (clones SC4, SC5, SC6, and SC9) had overlapping sequence and each hybridized to two bands of 3.4 kb and 4.4 kb on a Northern blot of keratinocyte RNA. Clone 80A was generated by 5' RACE from keratinocyte RNA. Clones 86C and 86A were generated by 3' RACE from keratinocyte RNA. All clones were sequenced except for the 3'-most 1 kb of clone 86A. Because these clones had overlapping sequence which was not represented in Gelnbank and they hybridized to keratinocyte mRNAs within the expected size range, they were suspected to represent the sciellin gene.

The cDNA inserts from plaque-purified clones were amplified by PCR using primers made to the lambda gt11 cloning site flanking sequence (PFO169: ACGACTCCTG-GAGCCCGTCAGTAT (SEQ ID NO:11), and PFO170: ACCAACTGGTAATGGTAGCGACCG) (SEQ ID NQ:12) and subdloned into pCR2.1 (Invitrogen) or the EcoRI site of pBluescript KS+ (Stratagene). Overlapping cDNA clones which further extended the sequence were generated by 5' and 3' RACE reactions using nested primers and the 5' and 3' RACE System kits (Gibco BRL) according to manufacturer's protocols (FIG. 1). The nested primers used for 5' RACE were MF79 (CTTCAGGGGTCACTTTGATGAGAT) (SEQ ID NO:13) and MF80 (ATCAAGGCTCTGGCCCCTCGTAAT) (SEQ ID NO:14). The nested primers used for 3' RACE were MF85 (AACAATCAGAGCCAAGACTTGGAC) (SEQ ID NO:15) and MF86 (GAAACACTAATCGAGACCAGAACCTGG) (SEQ ID NO:16).

DNA Sequencing and Computer Analysis cDNAs which were subcloned into pBluescript, pGEM (Promega) or pCR2.1 were sequenced using the Thermo Sequenase Radiolabeled Terminator Cycle Sequencing Kit (Arnersham) and $^{32}$P-ddNTPs. At least two independenit cDNA subclones were sequenced to rule out Taq polymerase-generated nucleotide substitutions. In some cases, PCR product bands were sequenced directly by cycle sequencing after excision from a TAE-EtBr agarose gel and purification using the QIAquick Gel Extraction Kit (Qiagen).

The sequencing project was analyzed using the Wisconsin Package Version 9.1 (Genetics Computer Group (GCG), Madison, Wisc.). Database comparisons were made using BLAST v2.0 (Altschul S. F. et al. (1977) *Nucleic Acids Res.* 25:3389–3402). The protein sequence was analyzed using the program PSORTII (Horton P. and Nakai K. (I1997) *Intelligent Systems for Molecular Biology* 5:147–152).

The full-length cDNA sequence of sciellin is 2347 bp, including 86 bp of 5'-untranslated sequence and 257 bp of 3'-untranslated sequence (FIG. 2). The nucleotide sequence surrounding the AUG initiator codon fits the consensus sequence for the initiation of translation by eukaryotic ribosomes (Kozak M. (1991) *J Cell Biol* 115:887–903). The 2004 bp open reading frame encodes a protein of about 668 amino acids having a molecular mass of about 75.3 kD, which is close to the 82 kD previously reported for the protein upon western blotting of cultured human keratinocyte extracts. The predicted isoelectric point of the unmodified protein as calculated from the sequence data was 10.09.

Protein Isolation of Sciellin

Sciellin protein was purified from human placenta using an immunoaffinity column made with polyclonal antiserum generated against a fulssion protein. In brief, human placentas were dissected to collect only the amniotic membrane. The placentas were then frozen in liquid nitrogen, ground in a Waring blender (Waring Product Div., New Hartford, Conn.) and resuspended in citric acid monohydrate 0.1 M (100 ml for 50 g of tissue) containing 625 mg/l of N-ethylmaleimide and 150 mg/l of phenylmethylsulphonyl fluoride). The suspension was incubated at 4° C. with stirring overnight. The soluble fraction was collected following centrifugation (30000×g, for 30 min) and precipitated by adding 0.3 M NaCl final and raising the pH to 5.0. The precipitated proteins were clllected following centrifugation (30000×g, 30 min) and redissolved into buffer A: 1501 mM NaCl, 2 mM EDTA, 10 mM Tris-HCl, pH 7.8 containing SDS 1%. At this point, the solution was boiled for 5 minutes, then 9 volumes of buffer A were added. The solution was then passed over a gelatin-Sepharose column (Pharmacia Fine Chemical, Piscatalay, N.J.) followed by an pAb SC4 immunoaffinity column. The columns were washed with PBS buffer and the elutions were done with 1M acetic acid.

Protein Sequencing of Sciellin

Protein sequencing was done according to Aebersold et al. (1987). Sciellin was eluted from the pAb SC4 affinity column and the fractions were concentrated by precipitation with 9 volumes of ethanol 100%. The material was then electrophoresed on a 7.5% SDS-page, stained briefly with Coomassie Blue 0.2%, destained in acetic acid 7%, methanol 10%. The band corresponding to sciellin was excised from the gel, washed in $H_2O$ and kept in acetonitrile 50% until sequenced.

The N-terminal amino acid was blocked. Sequence was obtained by mass spectrometry from two tryptic peptides. Briefly, the baind was incubated with trypsin and the resulting peptides were separated by HPLC and analyzed by matrix-assisted laser desorption time-of-flight mass spectrometry performed on a Finnigen Lasermat 2000 (Hemel, UK) (Chait B. T. and Kent S. B. (1992) *Science* 257:1885–1894). To obtain the N-terminal sequence, the material was blotted on a PVDF membrane (Bio-Rad Laboratories, Richmond, Calif.) stained with Ponceau-S and the band corresponding to sciellin was sequenced on the sequenator. The peptide sequences SSEQGLDEHINVSPK (SEQ ID NO:25) and QPLENLQAGDSIWIYR (SEQ ID NO:26) matched perfectly with the translated cDNA sequence from residues 443–457 and 635–650 (FIG. 3).

Structural Analysis of Sciellin

The amino acid sequence of sciellin is shown in FIGS. 2–3 and is 668 residues long. Comparison of the sciellin protein sequence with the Genbank database using the program BLAST showed that sciellin was a unique protein. The protein was generally hydrophilic and did not contain any regions likely to form either a signal peptide or a transmembrane domain, consistent with its cytoplasmic localization by immunohistochemistry.

The deduced sciellin protein sequence can be divided into three domains based upon potential structure and function predictions (such as those generated by the program Plotstructure (GCG)): an amino domain, a central domain comprised of repeating units, and a carboxyl domain containing a single LIM motif. Prolinre residues were evenly distributed throughout the molecule, except for an enriched "hinge" region before the first repeat unit, starting at residue 165.

Comparison of the encoded protein against the PROSITE database (Bairoch A. et al. (1997) *Nucleic Acids Res* 25:217–221) revealed that sciellin has sixteen potential N-glycosylation sites, five potential myristylation sites and thirty-five potential phosphorylation sites, including three cAMP- and cGMP-dependent protein kinase phosphorylation sites, twenty-two protein kinase C phosphorylation sites, nine casein kinase II phosphorylation sites, and one tyrosine kinase phosphorylation site. Western blots of large 2D gels of cultured keratinocyte extracts using 34d11 showed bands of 85.7 kD (PI 8.32), 86.1 kD (PI 8.72), 86.1 kD (PI 8.86) and 86.2 kD (PI 9.08) (HumaniKeratinocytes-NEPHGE Database, Danish Centre for Human Genome Research, http://biobase.dk/cgi-bin/celis). Post-translational phosphorylation of sciellin may explain the difference between the observed and calculated pI and Mr values of the protein.

Analysis of the sciellin protein sequence with the subcellular localization site prediction program PSORTII (Horton P. and Nakai K. (1997) *Intelligent Systems for Molecular Biology* 5:147–152) suggested that sciellin rnay be a nuclear protein, based upon the presence of four potential nuclear localization signals. However we have never found sciellin located in the nucleus by immunofluorescent staining of keratinocyte cell cultures, which presumably contain cells in all phases of the cell cycle (Champliaud M.F. et al. (1998) *J Invest. Dermtol.* In Press).

The program PEST-FIND (Rogers S. et al. (1986) *Science* 234:364–368) identified a potential PEST sequence at 326–339. PEST sequences are rich in Pro (P), Glu (E), Ser (S) and Thr (T) and are often flanked by clusters of positively charged residues. PEST sequences are believed to confer susceptibility to rapid intracellular proteolysis, resulting in an intracellular half life of less than two hours.

Analysis of Central Domain Repeats

The sciellin repeats are about 20 residues long and are characterized by a striking pattern of alternating stretches of hydrophobicity and hydrophilicity on hydropathy plots. There were 16 inexact repeat units from residues 231 to 543 of which 12 were 20 amino acids in length. The fourth, seventh, eighth, and tenth amino acid residues in the repeats were mainly hydrophobic, the fifth, ninth, thirteenth, and sixteenth charged and the second, ninth and sixteenth rich in Gln and Lys. The overall percentage of Gln and Lys in the repeat region of the molecule was identical to the remainder of the sequence. The twelfth position was rich in Pro which would allow for flexibility in the approximate center of the repeats. In plots of relative hydrophobicity, the repeats show up as having a pattern of alternating hydrophobic and hydrophilic stretches (FIG. 4). The hydrophobic stretches are predicted to form beta structures of 5–7 residues, terminating at the Pro residue.

The hydrophobic stretches are 5–7 residues long, and are predicted to form beta sheets. This is very similar to the parallel beta helix structure which has been described for the P22 tailspike protein and pectate lyase C (Yoder, M.D. et all (1993) *Science* 260:1503–1507). The crystal structure of the P22 tailspike protein demonstrates that each subunit of the homotrimer contains a large parallel beta helix. The beta helix of each strand is formed by short parallel beta sheets coiled into a large right-handed helix, similar to a rope coiled into a tidy cylinder. Each turn of the beta helix is comprised of between 16 and 22 residues. The hydrophobic side chains stack into the helix interior so the beta strands are arranged in stacks like rungs on a ladder. The charged and polar residues form a hydrophilic interface between adjacent beta helices in the homotrimer. The carboxyl domain of P22 tailspike protein is important for the association of monomers. By analogy, sciellin could form homotrimeric beta helices which become cross-linked by transglutami nase into very rigid protein girders, lending structural support to the cornified envelopes of stratum corneum cells. The presence of a PEST sequence could ensure that monomeric sciellin is rapidly degraded in the absence of crosslinking transglutaminases.

The repeats surrounding the amino acids LIKV were found in the repeat region of sciellin as shown in FIG. 3. The repeats involving G were few and short and NQG was found three times and GQS twice. However, the repeat IGQDPVK reported as a transglutaminase substrate in elaphin and the repeats AQEPVK and GQDKVK found to link elaphin to loricrin were not observed in sciellin. Also thl e sequence around glutamine 496 (EQQV) in involucrin, the preferential site of labeling by transglutaminase was not present in sciellin.

Analysis of Carboxy Terminal LIM Motif

The carboxyl domain of sciellin contained a single LIM motif consensus sequence (FIG. 5). The LIM domain has a characteristic arrangement of Cys and His residues which coordinate zinc ions into structures that function as protein-binding interfaces (Schmeichel K. L. and Beckerle M. C. (1994) *Cell* 79:211–219). In particular, the consensus sequence of the LIM motiff is as follows: $CX_2CX_{16-23}HX_2CX_2CX_2CX_{16-21}CX_{2-3}$(C,H,D) (SEQ ID NO:17). LIM motiffs have been identified in a number of proteins with diverse functions and subcellular locations, including transcription factors, and components of adhesion plaques and the actin-based cytoskeleton. A single LIM domain of roughly 56 amino acids folds into two independent structural domains, with the conservedi Cys and His residues coordinating two Zinc ions (Sanchez-Garcia I. and Rabbitts T. H. (1994) *Trends in Genet.* 10:315–320). All nine Cys residues in sciellin were found in this carbpxyl domain, starting at residue 601. These were not expected to form interchain crosslinks because sciellin has the same mobility in SDS-PAGE with and without treatment with a reducing agent.

Proteins containing LIM domains have been classified according to the number and position of LIM domains and the presence of other functional motifs, such as homeodomains (Taira M. et al. (1995) *Trends in Genet.* 11:431–432). Sciellin is a group 3 LIM protein as it has a single LIM domain in its carboxyl end. Other group 3 LIM proteins are known to interact with the cytoskeleton and might function in cell adhesiveness, intracellular signalling, and defining cell shape. This group includes zyxin, a low abundance phosphoprotein concentrated at adhesion plaques and associated with actin filament arrays (Beckerle M. C. (1986) *J. Cell Biol.* 103:1679–1687). Zyxin contains three LIM domains in its carboxyl end and these have been shown to mediate Izyxin binding to CRP (Crawford A. W. et al. (1994) *J. Cell Biol.* 124:117–127), which also contains two LIM domains. Zyxin binds a-actinin through a different functional domain. AbLIM (Roof D. J. et al. 1997) *J. Cell Biol.* 138:575–588) is an actin-binding LIM protein which localizes to adherens junctions in the retinal outer limiting membrane. Enigma is a LIM protein which binds to insulin receptors via a LIM domain recognizing a Tyr-containing tight turn structure on the receptor (Wu R. Y. and Gill G. N. (1994) *J. Biol. Chem.* 40:25082–25090).

Individual LIM domains can display distinct binding specificities. The conserved Cys and His residues coordinate zinc ions, folding the LIM domain into two loops. The sequences of the intervening loops may confer binding specificity. This distinct partner preference of a single LIM domain has been demonstrated in the protein zyxin. One of the three zyxin LIM domains is necessary and sufficient to direct specific binding of zyxin with CRP, but not with other LIM domain-containing proteins (Schmeichel K. L. and Beckerle M. C. (1994) *Cell* 79:211–219). It has also been demonstrated that a single LIM domain can interact with two other LIM domains as an adaptor element to promote the assembly and targeting of multiprotein complexes (Arber S. and Caroni P. (1996) *Genes and Devel* 10:289–300). The LIM domain of sciellin may be involved in homotypic or heterotypic associations and may function to localize sciellin to the cornified envelope, mediate the assembly of multiprotein structural complexes or regulate the activity of its protein partners.

Northern Blot Analysis of Sciellin mRNA Expression

Total RNA was isolated using the RNeasy (Qiagen) from human foreskin keratinocytes cultured in high calcium medium and also from post-partum human placentas, carefully dissected into amnion, chorion, villous and non-villous layers. 25 µg of RNA per lane were electrophoresed through a 1% agarose gel, blotted onto nitrocellulose and hybridized using the NorthernMax kit (Ambion) according to the enclosed protocols. 32P-dCTP-labelled probes were generated from gel-purified DNA using the Rediprime Random Primer Labelling Kit (Amersham). The probe for the keratinocyte and placenta blot was generated from the EcoRI insert of cDNA clone SC4. The probe for the 4.4 kb sciellin message was generated by 3' RACE from clone 86A using primer MF175 (GCAAGCGGGTGATAGTATTTGGAT) (SEQ ID NO:18).

Human Normal Tissue Blots I and II (Northern Territory Total RNA Blots, Invitrogen) were hybridized with a 32P-UTP-labelled antisense RNA probe made from pPO325 (Sciellin cDNA nt. 830–2310 subcloned into pBluescript II KS+) using the RNA Transcription Kit (Stratagene). The blots were hybridized and washed under stringent conditions using the NorthemMax Buffer System (Ambion), according to the supplied protocols.

Human sciellin cDNA probes hybridized to two messages of about 3.4 and 4.4 kb on Northern blots of both poly(A)+ RNA from stratified squamous epithelial tissues and amnion. A Northern blot of poly(A)+ RNA hybridized with a random-primed DNA probe demonstrated that human sciellin mRNAs are expressed in cultured keratinocytes and amnion, but not in carefully dissected villous chorion, decidua basalis or smooth chorion. Human Multiple Tissue Northerns (Invitrogen) were hybridized with an antisense RNA probe made from the sciellin cDNA clone pPO325. Sciellin mRNA shows limited expression in human tissues. Strong expression is detected in the esoIphagus, but not in stomach, intestine, colon, uterus, placenta, bladder, or adipose tissue or in heart, brain, kidney, liver, lung, pancreas, spleen, or muscle.

The reported sequence is believed to represent the short message. When PCR primers made to the sequences surrounding the initiator methionine and stop codons were used to amplify the complete coding region of the sciellin cDNA, only a single band was ever found. Both monoclonal and polyclonal antibodies recognized a single band on a Western blot, suggesting the difference in message sizes is not in the coding region. Multiple attempts at 5' RACE, using nested PCR primers which were derived from several different regions within the coding sequence always gave a single band corresponding in size to the reported 5' end. Multiple attempts at 3' RACE, also using nested primer's from different regions, resulted in two bands, corresponding to the reported 3' end and one which was 1 kb longer. The larger band, cDNA 86A (FIG. 1), was difficult to subclone and when sequenced directly from the PCR product gave a sequence identical to the short form clone 86C, including a polyadenylation signal and a poly(A)+ tail in the same position, and unreadable sequence 3' of this tail. It is not known if clone 86A has an additiorial poly(A)+ tail at its 3'-most end as this region remains unsequenced, but the utilization of alternative transcription termination signals is a well documented phenomenon (Pikkarainen T. et al. (1988) *J BioL Chem.* 263:6751–6758). When a portion of cDNA 86A (2.0–3.35 kb, FIG. 1) was used as a Northern probe it hybridized to both the 3.4 and 4.4 kb bands, although the 4.4 kb band signal intensity was much stronger than the 3.4 kb band intensity. Assuming that the size difference in mRNA bands is due to an additional 1 kb at the 3' end, one would expect that only 0.35 kb of the 86A probe could hybridize with the 3.4 kb band and all 1.35 kb of the probe could hybridize with the 4.4. kb band, resulting in significantly different hybridization intensities. This is consistent with the observed 86A Northern band intensities.

Northern probes derived from anywhere else in the sciellin cDNA hybridized to the two bands with roughly equal intensity. Therefore, the two message sizes observed for sciellin can be explained by the presence of two transcription termination signals whichl are 1 kb apart in the 3'-untranslated region.

Tissue Distribution of Sciellin mRNA Detected by In Situ Hybridization

Sense and antisense digoxigenin-RNA probes were transcribed from the plasmids pPOSC5 and pPOK5 using the RNA Transcription Kit (Stratagene) and DIG RNA labelling mix (Boehringer Mannheim Biochemicals). The RT-PCR amplification product of the keratin K5 MRNA from nt. 73–1076 (Lersch R. and Fuchs E. (1988) Mol. Cell. Biol 8:486–493) was subcloned into pBluescript KS+to create pPOK5, and clone SC5 was subloned into pBluescript KS+ to create pPOSC5. Ten (10) micron sections were cut from human foreskin which had been fixed in 4% paraformaldehyde and froz en in O.C.T. Compound (TissueTek). Tissue sections were hybridized overnight at 60° C. in a 50% formamide hybridization buffer. DIG was detected using anti-digoxigenin-alkaline phosphatase FAb fragments (Boehringer Mannheim Biochemicals) according to manufacturer's protocols.

In situ hybridization of human foreskin sections with a sciellin antisense probe made from clone SC5 showed that sciellin MRNA is expressed in the upper stratum spinosum and the stratum granulosum. In situ hybridization with a control keratin 5 antisense probe showed that the K5 mRNA is expressed primarily in the basal keratinocytes. Neither sciellin nor K5 sense probes hybridized to foreskin sections.

Expression of Recombinant Sciellin

Sciellin cDNA, corresponding to cDNA clone SC4 (FIG. 1), nucleotides 1120–1736, was amplified by RT-PCR from human differentiated keratinocyte RNA using adaptor primers PFO237 (GTTCCATATGGAAAATACCACTIGGAAAAAAAGAC) (SEQ ID NO:19) and PFO238 (TCCCGCGGTTACTTGGCTCC,AGTGTTAGAGCT) (SEQ ID NO:20) and subcloned into the NdeI and SacII sites of the T7 expression vector pET-15b (Novagen), which had been modified by replacement off the BamHI site with a SacII site (a gift of Manuel Koch). The resulting fusion protein con struct, pPO324, was transformed into Novablue (DE3) competent cells (Novagen) and the fusion protein SC4 was expressed and purified using the His-Bind Resin and His-Bind Bufferl System (Novagen) according to manufacturer's protocols. Polyclonal antiserum was raised in two rabbits by Charles River Pharmservices using 0.1 mg of SC4 fusion protein per injection.

Production of a Sciellin Specific Antibody and Immunohistochemical Localization

For Western blot analysis, a mouse monoclonali antibody to sciellin (34D11) and two polyclonal antibodies against sciellin were used. To pr iepare the polyclonal antibodies, rabbits were immunized with a sciellin fusion protein expressed from the equivalent of cDNA clone SC4 using the pET system (Novagen).

SDS-PAGE analysis of sciellin and electrophoretic transfer of protein to nitrocellulose with immunoblot analysis were performed as described in Laemmli, 1970 and Lunstrum et al., 1986, respectively. The appropriate HRP-conjugated IgG (ICN) was used as the secondary antibody. The polyclonal sera of both rabbits identified a band of 84 kD by Western blotting of lysis buffer extracts of cultured human keratinocytes, while the preimmune sera did not react. This band was identicall in mobility to the sciellin band identified by monoclonal 34d11.

Polyclonal antisera raised against a fusion prote in expressed from the sciellin cDNA stained tissue sections by indirect immunofluorescencei in a pattern identical to the pattern generated using the sciellin monoclonal antibody. Immnunohistochemical analysis was performed following standard techniques. The appropriate FITC-conjugated secondary antibody (Cappel) was used for indirect immunofluorescence on 10 mm sections fixed with acetone at –20° C. for 10 minutes. Immunofluorescent staining of normal human body and plantar skin using the SC4 antibody showed peripheral staining of keratinocytes in the granular and upper spinous layers of epidermis and the inner layer of the isthmus of the hair follicle, identical to the pattern observed with 34d11. Bovine and newborn mouse skin gave a similar pattern of staining. The stratified epithelium of the tongue, oral cavity, esophagus, vagina, bladder, ureter and cornea also reacted with theiantibody. The simple epithelium of mouse and bovine trachea, lung, kidney, liver, and small and large intestine, as well as non-epithelial tissues, did not stain with the antibody. These findings are identical to the previously reported tissue distribution of sciellin using 34d11. The exception was staining of bovine and human amnion, in which sciellin presumably plays a role in barrier function.

Chromosomal Localization and Radiation Hybrid Mapping of the Sciellin Gene

A 1.45 kb cDNA probe, pPO325, was biotinylated with dATP using the BRL BioNick labeling kit (15° C., 1 hr) (Heng H. H. Q. et al. (1992) Proc Natl Acad Sci USA 89:9509–9513). The procedure for FISH detection was performed according to Heng et al. (1992), supra, and Heng, H. H. Q. et al. (1992) Proc Natl Acad Sci USA 89:9509–9513. Briefly, slides were baked at 55° C. for 1 hour. After RNase treatment, the slides were denatured in 70% formamide in 2x SSC for 2 min. at 70° C. followed by dehydration with ethanol. Probes were denatured at 75° C. for 5 min. in a hybridization mix consisting of 50% formamide and 10% dextran sulfate and loaded on the denatured chromosomal slides. After overnight hybridization, slides were washed and detected as well as amplified. FISH signals and the DAPI banding pattern were recorded separately by taking photographs, and the assignment of the FISH mapping data with chromosomal bands was achieved by superimposing FISH signals with DAPI banded chromosomes (Heng, H. H. Q., and Tsui, L.-C. (1993) Chromosoma 102:325–332).

Based on FISH mapping, the sciellin gene was located to chromosome 13, band q22. Under the conditions used, probe pPO325 hybridized with 76% efficiency (among 100 mitotic figures, 76 showed signals on one pair of the chromosomes). Since DAPI banding was used to identify the specific chromosome, the assignment between signal from probe and the long arm of chromosome 13 was obtained. The detailed position was further determined based on the summary from 10 photos (FIG. 6). There was no additional locus picked by FISH detection under the conditions used.

To further characterized the Sciellin gene chromosomal location, the Stanford G3 Radiation Hybrid Mapping Panel (Research Genetics) was screened by PCR using two primer pairs derived from the sciellin genomic DNA sequence, MF122 (TTTGGAACCTTGGTTACTTCT) (SEQ ID NO:21) and MF124 (GGCTCTGAGACTAAAATAATGTCT) (SEQ ID NO:22), and MF79 (CTTCAGGGGTCACTTTGATGAGAT) (SEQ ID NO:23) and PF0280 (AGCGGCCAAATGGCTCTGAGAC) (SEQ ID NO:214). The G3 panel was also screened using two STS markers which were linked to Clouston's hidrotic ectodermal dysplasia (Clouston's HED), D13S141 and D13S175 (Research Genetics). These markers were ordered relative to the SHGC framework markers of the G3 RH map v2.0 using the statistical analysis program RHMAP (http://shgc-www.stanford.edu).

A search of the OMIM database for disorders which mapped in the proximity of chromosome 13 band q22, and which had a skin, nail and hair phenotype, as indicated by the immunofluorescent localization of sciellin, suggested that Clouston's HED could be a candidate disease for a disrupted sciellin gene. The phenotype of Clouston's HED includes dystrophic nails, hair defects, and palmoplantar hyperkeratosis. The gene disrupted in Clouston's HED was also mapped to chromosome band 13q and linkage analysis showed it was linked to the STS markers D13S175 and D13S141 (Kibar Z. et al. (1996) Hum. Mol. Genet. 5:543–547). Radiation hybrid mapping was used to determine if the sciellin gene also showed linkage to these same STS markers which are linked to HED. The Stanford G3 Radiation Hybrid Mapping Panel (Stewart E. A. et al. (11997) Genome Res. 7:422–433) was screened by PCR with markers derived from the scielliin gene, MF122/MF124 and MF79/PF0280, as well as the markers which were shown to be linked to Clouston's HED. MF122/MF124 was linked to the framework marker WI-457 at a distance of 14.56 cR and a L.O.D. score of 7.77, and MF79/PF0280 was linked to the framework marker WI-457 at a distance of 23.69 cR and a L.O.D. score of 5.86. D13S175 was linked to the framework marker SHGC-6104 and D13S141 was linked to the framework marker SHGC-37580 at a distance of 66.1 cR and a L.O.D. of 3.99. The sciellinlgene did not show linkage to the STS markers which were previously shown to be linked to Clouston's HED, therefore it is unlikely that HED is a candidate disease for a disrupted sciellin gene.

Analogs of Sciellin

Analogs can differ from naturally occurring sciellin in amino acid sequence or in ways that do not involve sequence, or both. Non-sequence modifications include in vivo or in vitro chemical derivatization of sciellin. Non-sequence modifications include changes in acetylation, methylation, phosphorylation, carboxylatio In, or glycosylation.

Preferred analogs include sciellin (or biologically active fragments thereof) whose sequences differ from the wild-type sequence by one orl more conservative amino acid substitutions or by one or more non-conservative amino acid substitutions, deletions, or insertions which do not abolish the sciellin biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequen ce. Also included are: analogs that include residues other than naturally occurring L-amino acids, e.g., D-amino acids or non-naturally occurring or synthetic amino acids, e.g., β or γ amino acids; and cyclic analogs.

Gene Therapy

The gene constructs of the invention can also be Iused as a part of a gene therapy protocol to deliver nucleic acids encoding either an agonistic or antagonistic form of a sciellin polypeptide. The invention features expression vectors for in vivo transfection and expression of a sciellin polypeptide in particular cell types so as to reconstitute the function of, or alternatively, antagonize the function of a sciellin polypeptide in a cell in which that polypeptide is misexpressed. Expression constructs of sciellin polypeptides, may be administered in any biologically effective carrier, e.g. any formulation or composition capable of effectively delivering the sciellin gene to cells in vivo. Approaches include insertion of the subject gene in viral vectors including recombinant retroviruses, adenovirus, adeno-associated virus, and herpes simplex virus-i, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g. a cDNA, encoding a sciellin polypeptide. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous gene's in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) Blood 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including epithelial cells, in vitro and/or in vivo (see for example Eglitis, et al. (1985) Science 230:1395–1398; Danos and Mulligan (1988) Prloc. Natl. Acad. Sci. USA 85:6460–6464; Wilson et al. (1988) Proc. Natl. Acad. Sci. USA 85:3014–3018; Armentano et al. (1990) Proc. NatL. Acad. Sci. USA 87:6141–6145; Huber et al. (1991) Proc. NatL. Acad. Sci. USA 88:8039–8043; Ferry et al. (1991) Proc. Natl. Acad. Sci. USA 88:8377–8381; Chowdhury et al. (1991) Science 254:1802–1805; van Beusechem et al. (1992) Proc. Natl. Acad. Sci. USA 89:7640–7644; Kay et al. (1992) Human Gene Therapy 3:641–647; Dai et al. (1992) Proc. NatL. Acad. Sci. USA 89:10892–10895; Hwu et al. (199$_3$) J. Immunol. 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berknerljet al. (1988) BioTechniques 6:616; Rosenfeld et al. (1991) Science 252:431–434; and Rosenfeld et al. (1992) Cell 68:143–155. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and conlcentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other, gene delivery vectors (Berkner et al. cited supra; Haj-Ahmand and Graham (1986) J. Virol. 57:267).

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1992) 158:97–129). It is also one of the few viruses that may integrate its DNA into non-dividing cells, and exhibits a high frequency of stable integration (see for example Flotte et al. (1992) Am. J. Respir. Cell. Mol. Biol. 7:349–356; Samulski et al. (1989) J. Virol. 63:3822–3828; and McLaughlin et al. (1989) J. Virol. 62:1963–1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251–3260 can be used to introduce DNA into cells. A variety of nucleic acids have been introduced into different cell types using AAV vectors (see for example Hermonat et al. (1984) Proc. Nati. Acdd. Sci. USA 81:6466–6470; Tratschin et al. (1985) Mol. Cell. Biol. 4:2072–2081; Wondisford et al. (1988) Mol. Endocrinol. 2:32–39; Tratschin et al. (1984) J. Virol. 51:611–619; and Flotte et al. (1993) J. Biol. Chem. 268:3781–3790).

In addition to viral transfer methods, such as those illustrated above, non-viral methods can also be employed to cause expression of a sciellin polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject sciellin gene by the targeted cell. Exemplary gene delivery systems of this type include liposomal derived systems, poly-lysine conjugates, and artificial viral envelopes.

In a representative embodiment, a gene encoding a sciellin polypeptide can be entrapped in liposomes bearing positive charges on their surface (e.g., lipofectins) and (optionally) which are tagged with antibodies against cell surface antigens of the target tissue (Mizuno et al. (1992) No Shinkei Geka 20:547–551; PCT publication WO91/06309; Japanese patent application 1047381; and European patent publication EP-A-43075).

In clinical settings, the gene delivery systems for the therapeutic sciellin gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is, more limited with introduction into the animal being quite localized. For example, the gene delivery vehicle can be introduced by catheter (see U.S. Pat. No. 5,328,470) or by Stereotactic injection (e.g. Chen et al. (1994) *PNAS* 91: 3054–3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

Transgenic Animals

The invention includes transgenic animals which include cells (of that animal) which contain a sciellin transgene and which preferably (though optionally) express (or misexpress) an endogenous or exogenous sciellin gene in one or more cells in the animal. The sciellin transgene can encode the wild-type form of the protein,lor can encode homologs thereof, including both agonists and antagonists, as well as antis ense constructs. In preferred embodiments, the expression of the transgene is restricted to specific subsets of cells, or tissues utilizing, for example, cis-acting sequences that control expression in the desired pattern. Tissue-specific regulatory sequences and conditional regulatory sequences can be used to control expression of the transgene in certain spatial patterns, e.g., to restrict production to the milk or other secreted product of the animal.

Production of Fragments and Analogs
Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Generation of Analogs: Production of Altered DNA and Peptide Sequences by Random Methods Amino acid sequence variants of a protein can be prepared by random mutagenesis of DNA which encodes a protein or a particular domain orlregion of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, *Technique* 1:11–15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, SA (1983) *Tetrahedron* 39:3; Itakura et al. (1981) *Recombinant DNA, Proc 3rd Cleveland Sympos. Macromolecules*, ed. AG Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Generation of Analogs: Production of Altered DNA and Peptide Sequences by Directed Mutagenesis Non-random or directed, mutagenesis techniques can be used to provide specific sequences or mutations in specific regions. These techniiques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the targetlresidue, or (3) inserting residues of the same or a different class adjacent to the located site,l or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect Ithe interaction of the amino acids with the surrounding aqueous environment in or outside the cell. Those domains demonstrating functional sensitivity to the substitutionslare then refined by introducing further or other variants at or for the sites of substitution. Thus, while the site for introducing an amino acid sequence variation is predetermined, the nature of the mutation per se need not be predetermined. For example, to optimize the perforrm ance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci. USA*, 75: 5765[1978]).

Cassette Mutagenesis

Another method for preparing variants, cassette inutagenesis, is based on the technique described by Wells et al. (*Gene*, 34:315[1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants. E.g., the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screenin Libraries of Peptide Fragments or Homologs Various techniques are known in the art for screening generated mutant gene products. Techniques for screening large gene libraries 6 fen include cloning the gene library into replicable expression vectors, transforming appropriate cells with the resulting library of vectors, and expressing the genes under conditions in which detection of a desired activity, e.g., in this case, binding to other sciellin subunits, assembly into a trimeric sciellin molecules, binding to natural ligands or substrates, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid (interaction trap) assays such as the system described above (as with the other screening methods described herein), can be used toi identify fragments or analogs (see e.g., U.S. Pat. No. : 5,283,317; PCT publication WO94/10300; Zervos et al. (1993) *Cell* 72:223–232; Madura et al. (1993) *J Biol Chem* 268:12046–12054; Bartel et al. (1993) *Biotechniques* 14:920–924; and Iwabuchi et al. (1993) *Oncogene* 8:1693–1696). These may include agonists, superagonists, and antagonists. (The subject protein and a protein it interacts with are used as the bait protein and fish proteins.). These assays rely on detecting the reconstitution of a functional transcriptional activator mediated by protein-protein interactions with a bait protein. In particular, these assays make use of chimeric genes which express hybrid proteins. The first hybrid comprises a DNA-binding domain fused to the bait protein. e.g., a sciellin molecule or a fragment thereof, e.g., the LIM domain. The second hybrid protein contains a transcriptional activation domain fused to a "fish" protein, e.g. an expression library, e.g., a keratinocyte expression library. If the fish and bait proteins are able to interact, they bring into close proximity the DNA-binding and transcriptional activator domains. This proximity is sufficient to cause transcription of a reporter gene which is operably linked to a transcriptional regulatory site which is recognized by the DNA binding domain, and expression of the marker gene can be detected and used to score for the interaction of the bait protein with another protein.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) *Bio/Technology* 9:1370 1371; and Goward et al. (1992) *TIBS* 18:136–140). In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell per mits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particulariphage is recovered from an affinity matrix in low yield, the phage can be amplified by another round of infection. The group of almost identical *E. coli* filamentous phages M13, fd., and fl are most often used in phage display libraries. Either of the phage glll or gVIII coat proteins can be used to generate fusion proteins without disrupting the ultimate packagi lhg of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; and Barbas et al. (1992) *PNAS* 89:4457–4461).

A common approach uses the maltose receptor of *E. coli* (the outer membrane protein, LamB) as a peptide fusion partner (Charbit et al. (1986) *EMBO* 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) *Vaccines* 91, pp. 387–392), PhoE (Agterberg, et al. (1990) *Gene* 88, 37–45), and PAL (Fuchs et al. (1991) *Bio/Tech* 9, 1369–1372), as well as large bacterial surface structures have served as vehicles for peptide display. Peptides can be fused tol pilin, a protein which polymerizes to form the pilus-a conduit for interbacterial exchange of genetic information (Thiry et al. (1989) *Appl. Environ. Microbiol.* 55, 984–993). Because of its role in interacting with other cells, the pilus provides a useful support for the presentation of peptides to the extracellular environment. Another large surface structure used for pieptide display is the bacterial motive organ, the flagellum. Fusion of peptides to the subunit protein flagellin offers a dense array of may peptides copies on the host cells (Kuwajima et al. (1988) *Bio/Tech.* 6, 1080–1083). Surface proteins of other bacterial species have also served as peptide fusion partners. Examples include the Staphylococcus protein A and the outer membrane protease IgA of Neisseria (Hansson et al. (1992) *J Bacteriol.* 174, 4239i4245 and Klauser et al. (1990) *EMBO J* 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein Lacd to form a link between peptide and DNA (Cull et al. (1992) *PNAS USA* 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of Ladl to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad. Sci. U.S.A.* 89–1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, plll and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. U.S.A.* 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are under-represlnted in the libraries (Gallop et al. (1994) *J Med. Chem.* 37(9):1233–1251). These particular biases are not a factor in the LacI display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available;phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding conplexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce, a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this forrnatior assay the peptides on individual clones for binding activity in a phage ELISA, or for binding specificity in a completion phage ELISA (Barret, et al. (1992) *Anal. Biochem* 204,357–364). To identify the sequences of the active peptides one sequences the DNA produced by the phagemid host.

Secondary Screens

The high through-put assays described above caln be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest and its respective ligand can be used to identify antagonists from a group of peptide fragments isolated though one of the primary screens described above.

Therefore, methods for generating fragments and analogs and testing them for activity are known in the art. Once the core sequence of interest: is identified, it is routine to perform for one skilled in the art to obtain analogs and fragments.

Peptide Mimetics

The invention also provides for reduction of the protein binding domains of the subject sciellin polypeptides to generate mimetics, e.g. peptide or non-peptide agents. See, for example, "Peptide inhibitors of human papillomavirus protein binding to retinoblastoma gene protein" European patent applications EP-412,762A and EP-B31,080A.

Non-hydrolyzable peptide analogs of critical residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), P-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

Antibodies

The invention also includes antibodies specific ally reactive with a subject sciellin polypeptides. Anti-protein/anti-peptide antisera or monoclonal antibodies can be made as described herein by using standard protocols (See, for example, *Antibodies. A Laboratory Manual* ed. by Harlow and Lane (Cold Spring Harbor Press: 1988)).

Antibodies which specifically bind sciellin epitopes can also be used in immunohistochemical staining of tissue samples in order to evaluate the abundance and pattern of expression of sciellin. Anti-sciellin antibodies can be used diagnostically in immuno-precipitation and immuno-blotting to detect and evaluate sciellin levels in tissue or bodily fluid as part of a clinical testing procedure.

Another application of antibodies of the present invention is in the immunological screening of cDNA libraries constructed in expression vectors such as λgt11, λgt18–23, λZAP, and λORF8. Messenger libraries of this type, halving coding sequences inserted in the correct reading frame and orientation, can produce fusion proteins. For instance, λgt11 will produce fusion proteins whose amino termini consist of 13-galactosidase amino acid sequences and whose carboxy termini consist of a foreign polypeptide. Antigenic epitopes of a subject polypeptide can then be detected with antibodies, as, for example, reacting nitrocellulose filters lifted from infected plates with antibodies of the invention. Phage, scored by this assay, can then be isolated from the infected plate. Thus, the presence of homologs can be detected and cloned from other animals, and alternate isoforms (including splicing variants) can be detected and cloned from human sources.

Other Embodiments

Included in the invention are: allelic variations; natural mutants; induced mutants; proteins encoded by DNA that hybridizes under high or low stringency conditions to a nucleic acid which encodes a polypeptide of SEQ ID NO:2 (for definitions of high and low stringency see *Current Protocols in Molecular Biology*, John Wiley & Sons, New York, 1989, 6.3.1–6.3.6, hereby incorporated by reference); and, polypeptides specifically bound by antisera to sciellin.

Nucleic acids and polypeptides of the invention includes those that differ from the sequences discolosed herein by virtue of sequencing errors in the disclosed sequences.

The invention also includes fragments, preferably biologically active fragments, or analogs of sciellin. A biologically active fragment or analog is one having any in vivo or in vitro activity which is characteristic of sciellin shown in SEQ ID NO:2, or of other naturally occurring sciellin, e.g., one or more of the biological activities described above. Especially preferred are fragments which exist in vivo, e.g., fragments which arise from post transcriptional processing or which arise from translation of alternatively spliced RNA's. Fragments include those expressed in native or endogenous cells, e.g., as a result of post-translational processing, e.g., as the result of the remoyal of an amino-terminal signal sequence, as well as those made in expression systemsl e.g., in CHO cells. Particularly preferred fragments are fragments, e.g., active fragments, which are generated by proteolytic cleavage or alternative splicing events.

Other embodiments are within the following claims.

What is claimed is:

1. A substantially pure nucleic acid comprising a nucleotide sequence which is at least 90% identical to the nucleotide sequence of SEQ ID NO:1, wherein the nucleic acid encodes a protein that (a) forms homotrimeric beta helices; (b) comprises a LIM domain; and (c) has a molecular weight between about 75.3 and 86.2 kDa.

2. A substantially pure nucleic acid comprising the nucleotide sequence of SEQ ID NO:1.

3. A nucleic acid that hybridizes under high stringency conditions to the full complement of the nucleotide sequence of SEQ ID NO:1.

4. The nucleic acid of claim 1, wherein the nucleic acid encodes a polypeptide that reacts with an antibody specific for a Sciellin polypeptide.

5. A substantially pure nucleic acid which encodes a fragment of SEQ ID NO:2 of at least 50 amino acids in length.

6. The nucleic acid of claim 1, wherein said nucleic acid comprises a nucleotide sequence which is at least 95% identical to the nucleotide sequence of SEQ ID NO:1.

7. The nucleic acid of claim 1, wherein said nucleic acid comprises a nucleotide sequence which is at least 98% identical to the nucleotide sequence of SEQ ID NO:1.

8. The nucleic acid of claim 1, wherein said nucleic acid comprises a nucleotide sequence which is at least 99% identical to the nucleotide sequence of SEQ ID NO:1.

9. A substantially pure nucleic acid which encodes an amino acid sequence which is at least 90% identical to the amino acid sequence of SEQ ID NO:2, wherein the nucleic acid encodes a protein that (a) comprises a LIM domain; (b) forms homotrimeric beta helices; and (c) has a molecular weight between about 75.3 and 86.2 kDa.

10. The nucleic acid of claim 9, wherein said nucleic acid encodes an amino acid sequence which is at least 95% identical to the amino acid sequence of SEQ ID NO:2.

11. The nucleic acid of claim 9, wherein said nucleic acid encodes an amino acid sequence which is at least 99% identical to the amino acid sequence of SEQ ID NO:2.

12. A substantially pure nucleic acid encoding the sciellin polypeptide of SEQ ID NO:2.

13. A substantially pure nucleic acid which encodes a fragment of the amino acid sequence of SEQ ID NO:2, wherein the fragment comprises a LIM domain.

14. A substantially pure nucleic acid which encodes a fragment of the amino acid sequence of SEQ ID NO:2, wherein the fragment comprises a domain capable of forming a homotrimeric beta-helix.

15. A vector comprising the nucleic acid of any of claims 1–14.

16. A cell comprising the nucleic acid of any of claims 1–14.

17. A method for manufacture of a Sciellin peptide comprising culturing the cell of claim 16 in a medium to express the Sciellin polypeptide.

* * * * *